| (12) | United States Patent | (10) Patent No.: | US 10,258,298 B2 |
|---|---|---|---|
| | Inoue et al. | (45) Date of Patent: | Apr. 16, 2019 |

(54) MEDICAL IMAGE SCANNING SYSTEM PROVIDED WITH BED AND ABNORMALITY DIAGNOSIS METHOD THEREOF

(71) Applicant: HITACHI, LTD., Tokyo (JP)

(72) Inventors: Yuta Inoue, Tokyo (JP); Mikio Mochitate, Tokyo (JP); Kenya Sakanaka, Tokyo (JP)

(73) Assignee: HITACHI, LTD., Tokyo (JP)

( * ) Notice: Subject to any disclaimer, the term of this patent is extended or adjusted under 35 U.S.C. 154(b) by 897 days.

(21) Appl. No.: 14/771,727

(22) PCT Filed: Mar. 13, 2014

(86) PCT No.: PCT/JP2014/056655
§ 371 (c)(1),
(2) Date: Aug. 31, 2015

(87) PCT Pub. No.: WO2014/156680
PCT Pub. Date: Oct. 2, 2014

(65) Prior Publication Data
US 2016/0007939 A1 Jan. 14, 2016

(30) Foreign Application Priority Data

Mar. 29, 2013 (JP) ................................ 2013-072103

(51) Int. Cl.
*A61B 6/03* (2006.01)
*A61B 6/04* (2006.01)
(Continued)

(52) U.S. Cl.
CPC .......... *A61B 6/0457* (2013.01); *A61B 6/0407* (2013.01); *A61B 6/10* (2013.01);
(Continued)

(58) Field of Classification Search
CPC .......... A61B 6/035; A61B 6/10; A61B 6/0407
See application file for complete search history.

(56) References Cited

U.S. PATENT DOCUMENTS

| 4,071,222 A | * | 1/1978 | Wright | ................. | B66F 7/0625 |
| | | | | | 254/124 |
| 4,449,262 A | * | 5/1984 | Jahsman | ................ | A61G 7/002 |
| | | | | | 248/421 |

(Continued)

FOREIGN PATENT DOCUMENTS

| JP | S59-146394 U | 9/1984 |
| JP | H09-110387 A | 4/1997 |

(Continued)

OTHER PUBLICATIONS

Dec. 5, 2017 Japanese Office Action issued in Japanese Patent Application No. JP 2015-508280.

(Continued)

*Primary Examiner* — David J Makiya
*Assistant Examiner* — Soorena Kefayati
(74) *Attorney, Agent, or Firm* — Oliff PLC

(57) ABSTRACT

A medical image scanning system includes a top plate on which an object is placed, a drive screw shaft, and a fall prevention unit. The fall prevention unit includes a load support nut that is threadedly engaged with the drive screw shaft and to which the load of the top plate is applied; a fall prevention nut that is arranged below the load support nut and is threadedly engaged with the drive screw shaft; a rotation prevention mechanism that prevents the rotation of the load support nut; and a detent mechanism that performs the turning stop of the fall prevention nut and releases the turning stop of the fall prevention nut when the threaded engagement between the drive screw shaft and the load support nut is disconnected.

4 Claims, 22 Drawing Sheets

(51) Int. Cl.
*A61B 6/10* (2006.01)
*B66F 7/06* (2006.01)

(52) U.S. Cl.
CPC ............ *B66F 7/065* (2013.01); *B66F 7/0608*
(2013.01); *A61B 6/032* (2013.01); *A61B 6/035*
(2013.01)

(56) References Cited

U.S. PATENT DOCUMENTS

| | | | | |
|---|---|---|---|---|
| 4,582,310 | A * | 4/1986 | Hahn | A61G 13/06 254/122 |
| 6,217,214 | B1 * | 4/2001 | Cabral | A61B 6/0421 378/196 |
| 6,234,034 | B1 * | 5/2001 | Ando | F16H 25/2472 187/267 |
| 7,669,493 | B2 * | 3/2010 | Hoth | A61B 6/0457 254/124 |
| 2001/0007588 | A1 * | 7/2001 | Iizuka | A61B 6/04 378/209 |
| 2005/0039643 | A1 * | 2/2005 | Dailey | A61B 6/0407 108/132 |
| 2007/0012112 | A1 * | 1/2007 | Kim | G01H 9/004 73/594 |
| 2007/0079443 | A1 * | 4/2007 | Hoth | A61B 6/0457 5/601 |
| 2008/0047068 | A1 * | 2/2008 | Zakrzewski | A61B 6/0457 5/611 |
| 2008/0081985 | A1 * | 4/2008 | Zheng | A61B 6/032 600/407 |
| 2008/0197279 | A1 * | 8/2008 | Kang | B66F 7/065 250/306 |
| 2009/0179757 | A1 * | 7/2009 | Cohn | G09F 3/0376 340/542 |
| 2010/0287703 | A1 * | 11/2010 | Zapata | A61B 6/0457 5/601 |
| 2010/0325797 | A1 * | 12/2010 | Horne | A61B 13/06 5/611 |
| 2011/0259429 | A1 * | 10/2011 | Whipps | E02B 7/36 137/1 |
| 2012/0067176 | A1 * | 3/2012 | Ota | B23P 19/006 81/57.37 |
| 2013/0111668 | A1 * | 5/2013 | Wiggers | A61B 6/0457 5/608 |
| 2013/0174341 | A1 * | 7/2013 | Shang | A61B 6/0407 5/611 |
| 2013/0312181 | A1 * | 11/2013 | Jackson | A61B 6/0407 5/601 |
| 2014/0033432 | A1 * | 2/2014 | Marle | A61G 7/1057 5/601 |
| 2014/0033433 | A1 * | 2/2014 | Kimishima | A61B 6/0407 5/601 |
| 2014/0208509 | A1 * | 7/2014 | Zhang | A61B 6/0407 5/601 |
| 2015/0020313 | A1 * | 1/2015 | Shibata | A61B 6/0407 5/610 |

FOREIGN PATENT DOCUMENTS

| | | |
|---|---|---|
| JP | H09-300246 A | 11/1997 |
| JP | 2000-095481 A | 4/2000 |
| JP | 2000-199028 A | 7/2000 |
| JP | 2002-011003 A | 1/2002 |
| JP | 2002-174319 A | 6/2002 |
| WO | 2010/098232 A1 | 9/2010 |

OTHER PUBLICATIONS

Apr. 22, 2014 International Search Report issued in International Patent Application No. PCT/JP2014/056655.

* cited by examiner

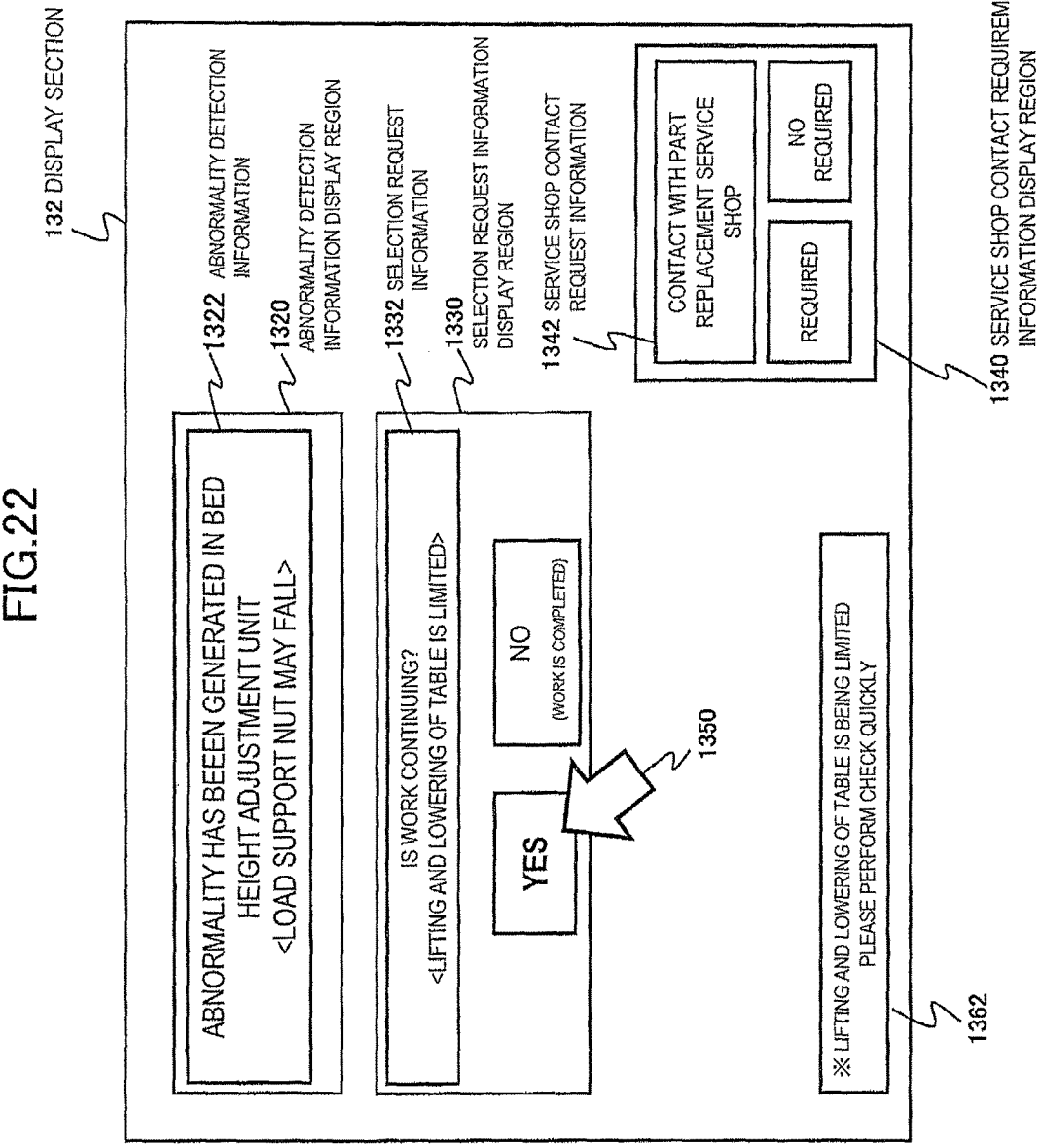

MEDICAL IMAGE SCANNING SYSTEM PROVIDED WITH BED AND ABNORMALITY DIAGNOSIS METHOD THEREOF

TECHNICAL FIELD

The present invention relates to a medical image scanning system provided with a bed.

BACKGROUND ART

In the related art, in beds which are used for medical image scanning systems and on which an object is placed, for example, a mechanism in which an object is placed on a top plate and lifting and lowering movement is performed by the driving of arms that support the top plate has been adopted.

In this type of medical image scanning system provided with a bed on which an object is placed, for example, as illustrated in PTL 1, using a bed device for medical image scanning that includes a base, a table, and an arm portion having a lifting and lowering mechanism for a table, and lifts and lowers the table through the driving of this arm portion is suggested.

CITATION LIST

Patent Literature

[PTL 1] Pamphlet of International Publication No. 2010/098232

SUMMARY OF INVENTION

Technical Problem

PTL 1 has the features of the invention from different viewpoints, and does not suggest a failure or the like of the lifting and lowering mechanism at all.

In scanning work in the medical image scanning systems, it is very important to maintain an object's safety. For example, objects include sick persons, elderly people, and people that require emergency care in addition to healthy persons, and it should be taken into consideration that such people use the medical image scanning systems. More consideration of preventing a shock from being given to an object, such as safety measures, especially, prevention of falling when being placed on a bed, compared to healthy persons are required for such people.

An object of the invention is to provide a medical image scanning system provided with a bed that can further improve an object's safety.

Solution to Problem

According to the invention, there is provided a medical image scanning system provided with a bed, the medical image scanning system including a top plate on which an object is placed, an arm that supports the top plate, a drive screw shaft, a fall prevention unit including a load support nut that is threadedly engaged with the drive screw shaft and to which the load of the top plate is applied, and a fall prevention nut that is arranged below the load support nut and is threadedly engaged with the drive screw shaft, a drive unit that rotates the drive screw shaft to change a distance from the fall prevention unit, thereby changing the height of the top plate, a scanning unit that performs scanning for obtaining a medical image of the object, a display section that displays the medical image, and a control unit that controls the drive unit to adjust the height of the top plate, and controls the scanning unit to perform scanning for obtaining a medical image, in which the fall prevention unit includes a detent mechanism that performs the turning stop of the fall prevention nut and that releases the turning stop of the fall prevention nut when the threaded engagement between the drive screw shaft and the load support nut is disconnected.

Advantageous Effects of Invention

According to the invention, it is possible to provide a medical image scanning system provided with a bed that can further maintain an object's safety.

BRIEF DESCRIPTION OF DRAWINGS

FIG. 22 is a view illustrating screen display at the time of the abnormality diagnosis of the medical image scanning system in FIGS. 20 and 21.

DESCRIPTION OF EMBODIMENTS

Figure 1:
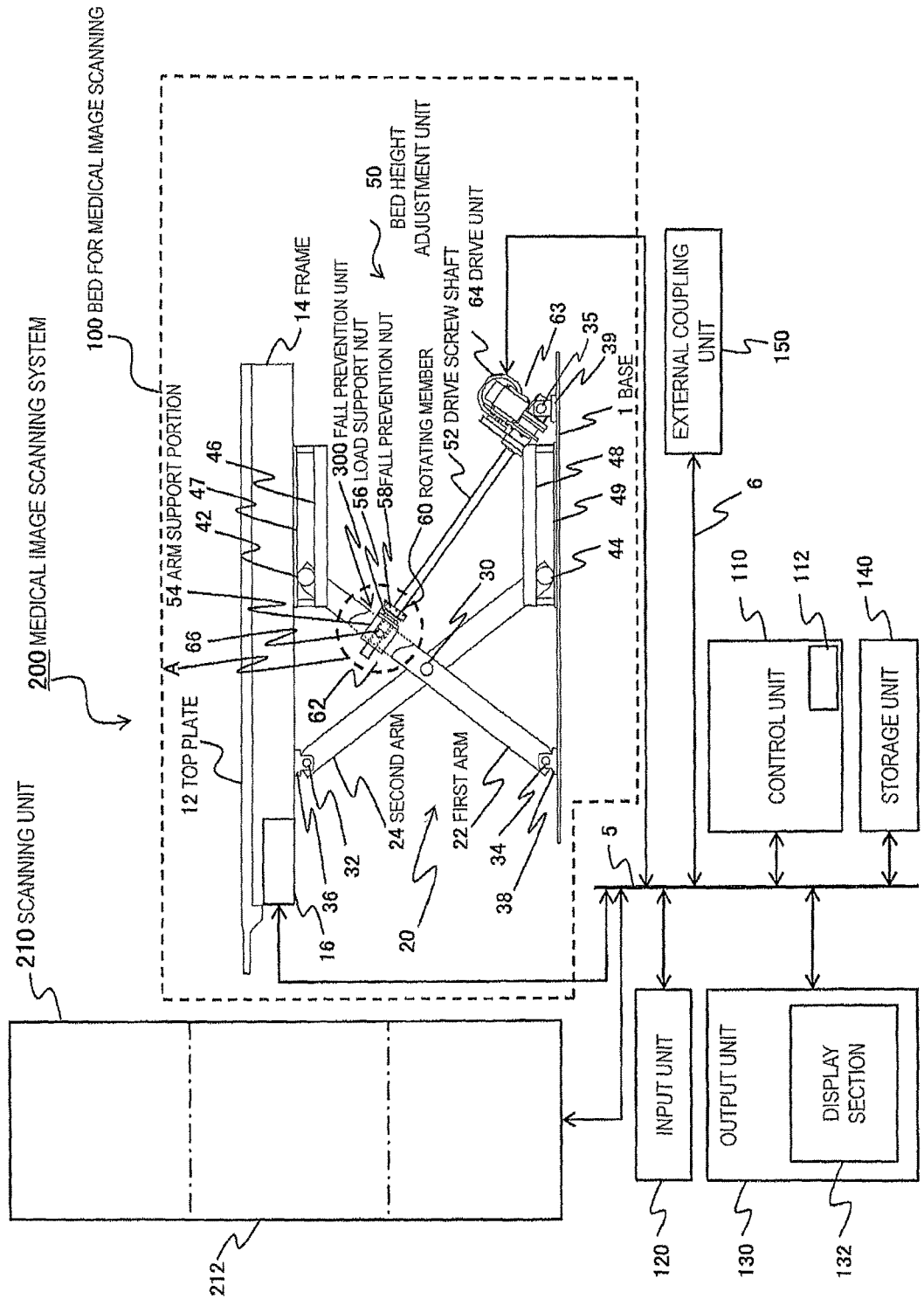
FIG. 1 is a schematic view illustrating an overall configuration of a medical image scanning system provided with a bed on which an object is placed, in an embodiment of the invention.

Hereinafter, beds for medical image scanning of embodiments of the invention will be described with reference to the accompanying drawings.

In addition, in the accompanying drawings, the same components are designated by the same reference numerals, and the repeated description thereof will be omitted. Additionally, in the beds for medical image scanning of the embodiments of the invention to be described below, a case where the beds for medical image scanning are applied to a system that performs X-ray CT scanning will be described. However, if a configuration to which the beds for medical image scanning of the present embodiments is provided, the beds can also be applied to other systems. Additionally, in the beds for medical image scanning of the embodiments of the invention to be described below, the load from a top plate is received by a load support nut of a fall prevention unit to be described below, and the height adjustment of the top plate is performed by changing the distance from a drive unit to the fall prevention unit depending on the rotation of a screw of a drive screw shaft.

Embodiment 1

FIG. 1 is a schematic view illustrating an overall configuration of a medical image scanning system provided with a bed on which an object is placed, in an embodiment of the invention. The example of FIG. 1 is an example in which a medical image scanning system 200 consists of an X-ray CT scanning device.

The medical image scanning system 200 of the present embodiment includes a scanning unit 210 that has an X-ray tube assembly and an X-ray detector (not illustrated) mounted thereon, rotates around an object, irradiates an object with X-rays, detects the X-rays transmitted through the object to transmit transmitted X-ray signals, a control unit 110 that has an image processor (not illustrated) that receives the transmitted X-ray signals transmitted from the scanning unit 210, and generates a reconstruction image, and controls an X-ray CT scanning system to perform X-ray scanning in accordance with scanning conditions input by an operator, an input unit 120 for inputting various instructions to the control unit 110, an output unit 130 including the display sections 132, such as a display that displays the reconstruction image generated by the image processor, and a storage unit 140 that stores information, including the generated reconstruction image and scanning programs.

In the medical image scanning system 200 having the above configuration, the X-ray scanning of an object is performed by placing the object on a top plate 12, horizontally moving the top plate 12 by the driving of a top plate drive unit 16, and arranging the top plate into an opening 212 of the scanning unit 210.

The control unit 110 includes a main storage unit 112, and is adapted to be able to store information on computation required for various control in the main storage unit 112, thereby performing computational processing at a high speed.

Communication of signals and information of the control unit 110, the input unit 120, the output unit 130, the storage unit 140, and the scanning unit 210 is performed via communication unit 5, such as buses. Additionally, these units are connected to an external coupling unit 150 coupled to an external server, an external instrument, or the like via an external transmission means 6, and is adapted to be able to perform transfer of signals and information with the external instrument.

The control unit 110 performs the output control of the output unit 130, the control of scanning of the scanning unit 210, and the input control of the input unit 120 via the communication unit 5, and performs the drive control of the top plate drive unit 16 to be described below, and the drive control of a bed height adjustment unit 50.

Additionally, the medical image scanning system 200 of the present embodiment includes the top plate 12 on which an object (not illustrated) is placed, a drive screw shaft 52, and a fall prevention unit 300.

The fall prevention unit 300 includes a load support nut 56 that is threadedly engaged with the drive screw shaft 52 and to which the load of the top plate 12 is applied; a fall prevention nut 58 that is arranged below the load support nut 56 and is threadedly engaged with the drive screw shaft 52; a rotation prevention mechanism 55 (refer to FIG. 3) that prevents the rotation of the load support nut 56; and a detent mechanism 57 (refer to FIG. 4) that performs the turning stop of the fall prevention nut 58 and that releases the turning stop of the fall prevention nut 58 when the threaded engagement between the drive screw shaft 52 and the load support nut 56 is disconnected.

Additionally, the medical image scanning system 200 of the present embodiment includes a drive unit 64 that rotates the drive screw shaft 52 to change the distance from the fall prevention unit 300, thereby changing the height of the top plate 12. Additionally, the medical image scanning system 200 of the present embodiment, as described above, includes the scanning unit 210 that performs scanning for obtaining a medical image of an object, and a control unit 110 that controls the scanning unit 210 to perform scanning for obtaining a medical image. The control unit 110 also performs controlling of the drive unit 64 to adjust the height of the top plate 12.

Additionally, in the medical image scanning system 200 of the present embodiment, the turning stop of the fall prevention nut 58 is released and the fall prevention nut 58 rotates along with the rotation of the drive screw shaft 52, in a state where the threaded engagement between the drive screw shaft 52 and the load support nut 56 is disconnected.

The configuration of a bed 100 (hereinafter referred to as a bed 100 for medical image scanning) that is provided in the medical image scanning system 200 of the present embodiment and has an object placed thereon, will be described below in detail.

The top plate 12 is supported by a frame 14, and the horizontal movement thereof relative to the frame 14 is performed by the driving of the top plate drive unit 16.

Additionally, the bed height adjustment unit 50 includes the drive screw shaft 52 that has one end 66 rotatably supported, an arm support portion 54 that is rotatably fixed to an arm 20, the load support nut 56 that supports the arm support portion 54 and is threadedly engaged with the drive screw shaft 52, the fall prevention nut 58 that faces the load support nut 56 and is threadedly engaged with the drive screw shaft 52, and the detent mechanism 57.

The arm 20 provided between the base 1 and the top plate 12 consists of a pantograph type structure, and is constituted of the base 1 and two pantograph arms (not illustrated) that are broadened and narrowed along a longitudinal direction of the top plate 12 and are provided in parallel. The two pantograph arms intersect each other in a substantially X-shape, and are rotatably coupled together by a center pin 30 that is a coupler at the intersecting point.

The two pantograph arms, that is, a first arm 22 and a second arm 24 intersect each other in a substantially X-shape, and are rotatably coupled together by the center pin 30 at the intersecting point. Since the center pin 30 is shared by the two pantograph arms, the two pantograph arms are moved and bent in an interlocking manner.

Additionally, a lower end of the first arm 22 is coupled to an upper surface of the base 1 via a bearing 38 fixed to a rotating shaft 34 and the base 1, and is rotatable and fixed without moving in broadening and narrowing directions of two pantograph arms. Additionally, an upper end of the first arm 22 is coupled to the frame 14 via a movement shaft 42 and a movement shaft guide portion 46, and is made rotatable and made movable along the guide groove 47 in the broadening and narrowing directions of the two pantograph arms.

In contrast, a lower end of the second arm 24 is coupled to the base 1 via a movement shaft 44 and a movement shaft guide portion 48, and is made rotatable and made movable along a guide groove 49 in the broadening and narrowing directions of the two pantograph arms. Additionally, an upper end of the second arm 24 is coupled to the frame 14 via a bearing 36 fixed to a rotating shaft 32 and the frame 14, and is rotatable and fixed without moving in the broadening and narrowing directions of the two pantograph arms.

Additionally, the drive unit 64 of the bed height adjustment unit 50 is constituted of a motor (not illustrated) and a gear driven by the motor, and has a structure in which the drive screw shaft 52 is rotated on the basis of the driving power of the motor by connecting the drive screw shaft 52 to the gear. Here, the drive screw shaft 52 has one end 63 coupled to the upper surface of the base 1 via a bearing 39 fixed to the drive unit 64, a rotating shaft 35, and the base 1, and is rotatable and is fixed without moving in the broadening and narrowing directions of the two pantograph arms.

Figure 2:
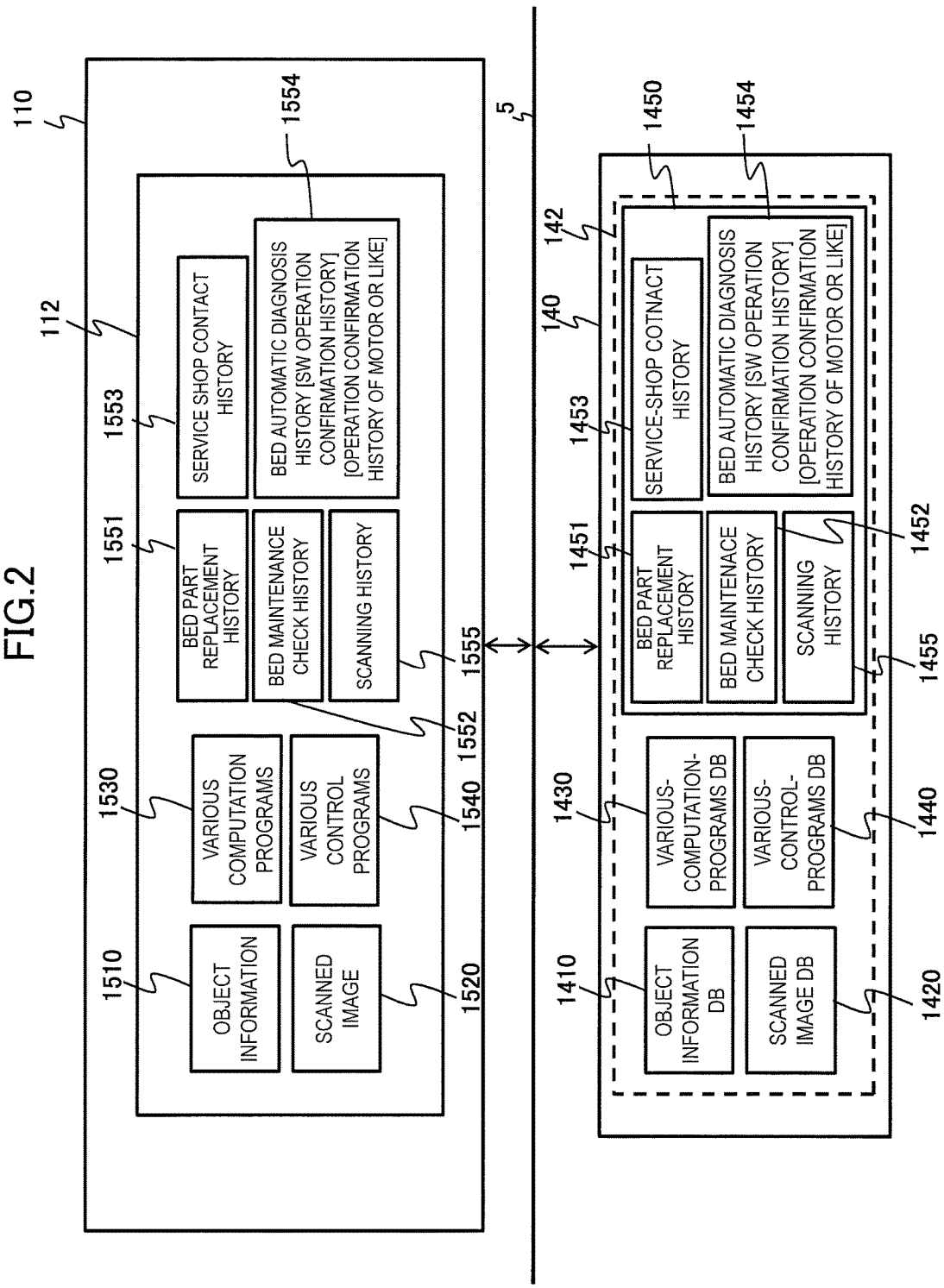
FIG. 2 is a view illustrating the structure of a database stored in a storage unit of the medical image scanning system of FIG. 1.

FIG. 2 is a view illustrating the structure of a database stored in the storage unit of the medical image scanning system of FIG. 1. Hereinafter, the database stored in the storage unit 140 will be described. A database 142 (hereinafter called DB for short) consisting of various kinds of data is stored in the storage unit 140, and includes an object information DB 1410 including object information, such as the names, height, and weight of objects, a scanned image DB 1420 including information on scanned images generated by the X-ray scanning or the like, a various-computation-programs DB 1430 including information on programs that perform various kinds of computation, such as image processing, a various-control-programs DB 1440 that performs various kinds of control, such as the scanning unit 210, the top plate drive unit 16, and the drive unit 64, and a history information DB 1450 including various kinds of history information.

Additionally, the history information DB 1450 consists of an information group 1451 of the bed part replacement history, an information group 1452 of the bed maintenance check history, an information group 1453 of the maintenance or contact history with service shops of parts, an information group 1454 of the bed automatic failure-diagnosis work history to be described below, an information group 1455 of the object scanning work history, and the like.

The control unit 110 reads information, including object information 1510, scanned images 1520, various computation programs 1530, various control programs 1540, information 1551 on bed part replacement history, information 1552 on bed maintenance check history, information 1553 on the maintenance or contact history with service shops of parts, information 1554 on the bed automatic failure-diagnosis work history to be described below, information 1555 on the object scanning work history, and the like, via the communication unit 5, from the above DB of the storage unit 140, and temporarily stores the information in the main storage unit 112, thereby generating signals for processing information at a high speed and performing various kinds of control, and performing respective kinds of control.

Figure 3:
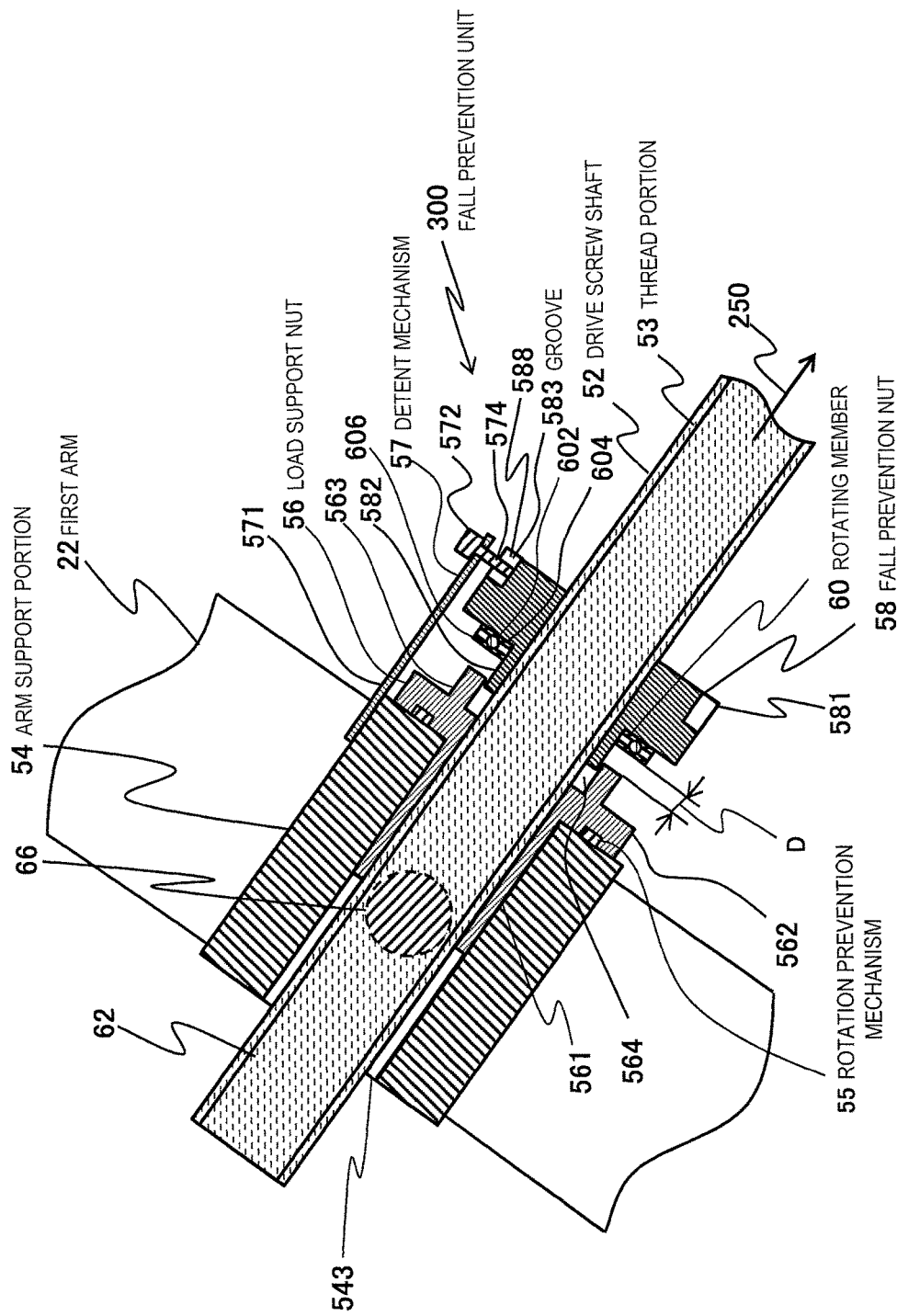
FIG. 3 is a longitudinal sectional view illustrating a detailed configuration of a fall prevention unit of the bed of the medical image scanning system of FIG. 1.

FIG. 3 is a longitudinal sectional view illustrating a detailed configuration of the fall prevention unit of the bed of the medical image scanning system of FIG. 1. The configuration of the fall prevention unit 300 of the bed height adjustment unit 50 of the bed 100 for medical image scanning of the present embodiment will be described below in detail. FIG. 3 illustrates a view of an enlarged portion of the region A enclosed by a dashed line illustrated in FIG. 1.

The bed height adjustment unit 50 includes the fall prevention unit 300, and extends and retracts the two above pantograph arms to perform the lifting and lowering movement of the top plate 12. The fall prevention unit 300 consists of the arm support portion 54 that is provided between the two above pantograph arms, a coupling portion 66 that rotatably couples both the pantograph arms and side surfaces of the arm support portion 54, respectively, the load support nut 56 that is fitted into an opening 543 of the arm support portion 54 and supports the arm support portion 54, the fall prevention nut 58 that is provided to face the load support nut 56, the detent mechanism 57 that is fixed to the arm support portion 54 and performs the turning stop of the fall prevention nut 58 in a detent 572, the drive screw shaft 52 threadedly engaged with the load support nut 56 and the fall prevention nut 58, and a rotating member 60 that is provided between the load support nut 56 and the fall prevention nut 58, and transmits the load from the load support nut 56 to the fall prevention nut 58 indirectly at the time of the falling of the load support nut 56.

Since the arm support portion 54 has the above-described structure, the arm support portion 54 can be rotated with the coupling portion 66 as an axis without moving in the longitudinal direction of the first arm 22. Additionally, the arm support portion 54 receives the load from the above two pantograph arms, that is, the arms 20, via the coupling portion 66.

The load support nut 56 is formed with a female thread portion (not illustrated) threadedly engaged with the drive screw shaft 52, and is constituted of a smaller-diameter fitting portion 561, a holder 562 that is made to have a larger diameter than the fitting portion 561 and is formed with a flange surface 565, and a protruding portion 563 that is made to have a smaller external diameter than the holder 562, is made to have a larger internal diameter than the nominal diameter of the female thread portion, is formed with a space 564, and protrudes in an axial direction.

The load support nut 56 is fixed such that the fitting portion 561 is fitted into the opening 543 of the arm support portion 54 and the load support nut 56 itself is not rotated. That is, the turning of the load support nut 56 is stopped by the arm support portion 54. Specifically, for example, by welding the fitting portion 561 or the holder 562 and the arm support portion 54, respectively, or by providing irregular portions in the holder 562 and the arm support portion 54, respectively, to fit and fix them to each other as illustrated, the turning stop is performed by the rotation prevention mechanism 55 that prevents the rotation of the load support nut 56. The load support nut 56 fitted into the opening 543 receives the load from the arms 20 via the arm support portion 54, with flange surface 565.

The load support nut 56 having the above structure moves linearly in the axial direction of the drive screw shaft 52, while the load support nut 56 itself receives the load of the arm support portion 54 without being rotated by the rotation of the drive screw shaft 52. Through the linear movement of the drive screw shaft 52 of the load support nut 56 in the axial direction, the broadening and narrowing movement of the arms 20 is performed, and the lifting and lowering movement of the top plate 12 is performed.

The detent mechanism 57 of the fall prevention unit 300 is constituted of a support portion 571 that is fixed to the arm support portion 54 and supports the detent 572, and the detent 572 having an end 574 that is arranged within a groove 583 provided in the fall prevention nut 58 and is locked to a lateral portion 588 of the groove 583. For example, a pin as illustrated is used as the detent 572. In this way, an engaging portion is constituted of the groove 583 that is a first member and the detent 572 that is a second member, which are engaged with each other and the turning of the fall prevention nut 58 is stopped by the groove 583 and the detent 572 having such a configuration being brought into an engaged state.

Therefore, the medical image scanning system 200 of the present embodiment includes an engaging portion consisting of the first member 583 and the second member 572 that are engaged with each other, the first member 583 of the engaging portion is provided at the fall prevention nut 58, the second member 572 of the engaging portion is supported so as to move together with the load support nut 56, and the first member 583 and the second member 572 are brought into the engaged state, whereby the turning of the fall prevention nut 58 is stopped. Additionally, as the threaded engagement between the drive screw shaft 52 and the load support nut 56 is disconnected, the load support nut 56 approaches the fall prevention nut 58, thereby the second member 572 of the engaging portion moves together with the load support nut 56, a fitting state between the first member 583 and the second member 572 of the engaging portion of the detent mechanism 57 is released, and the turning stop of the fall prevention nut 58 is released.

Here, the engaging portion may be configured by providing a convex portion on the fall prevention nut 58 and fitting this convex portion into a concave portion provided in the support portion. That is, the engaging portion in which the first member is the convex portion and the second member is the concave portion may be configured.

The fall prevention nut 58 consists of a head 581, and a protruding portion 582 made to have a smaller diameter than the head 581. Additionally, a plurality of the grooves 583 in which the lateral portion 588 is formed in the direction of a central axis are intermittently formed in a circumferential direction in the head 581 of the fall prevention nut 58. Also, the end 574 of the detent 572 is locked to the lateral portion 588 of one groove 583 as described above, and is made movable in the direction of the central axis.

Here, the reason why the plurality of grooves 583 are formed is because the turning stop of the fall prevention nut 58 can be easily performed by selecting and guiding a groove near the end 574 of the detent 572 of the detent mechanism 57 from the plurality of grooves 583 depending on the state of the threaded engagement of the fall prevention nut 58 with the drive screw shaft 52.

Accordingly, even if the fall prevention nut 58 receives the rotary power based on the rotation of the drive screw shaft 52, the fall prevention nut cannot be rotated by the end 574 of the detent 572 being locked to the lateral portion 588. That is, the fall prevention nut 58 is brought into a state where the turning thereof is stopped by the detent mechanism 57, similar to the load support nut 56. Additionally, the groove 583 of the fall prevention nut 58 has a shape that opens on a lower side in the direction of the central axis, that is, on the end 63 side of the drive screw shaft 52.

Additionally, a distance is provided between the above-described load support nut 56 and the fall prevention nut 58, and a distance D is provided between the load support nut 56 and the rotating member 60. By adopting this configuration, the load of the arms 20 received via the arm support portion 54 is received by the load support nut 56.

Figure 4:
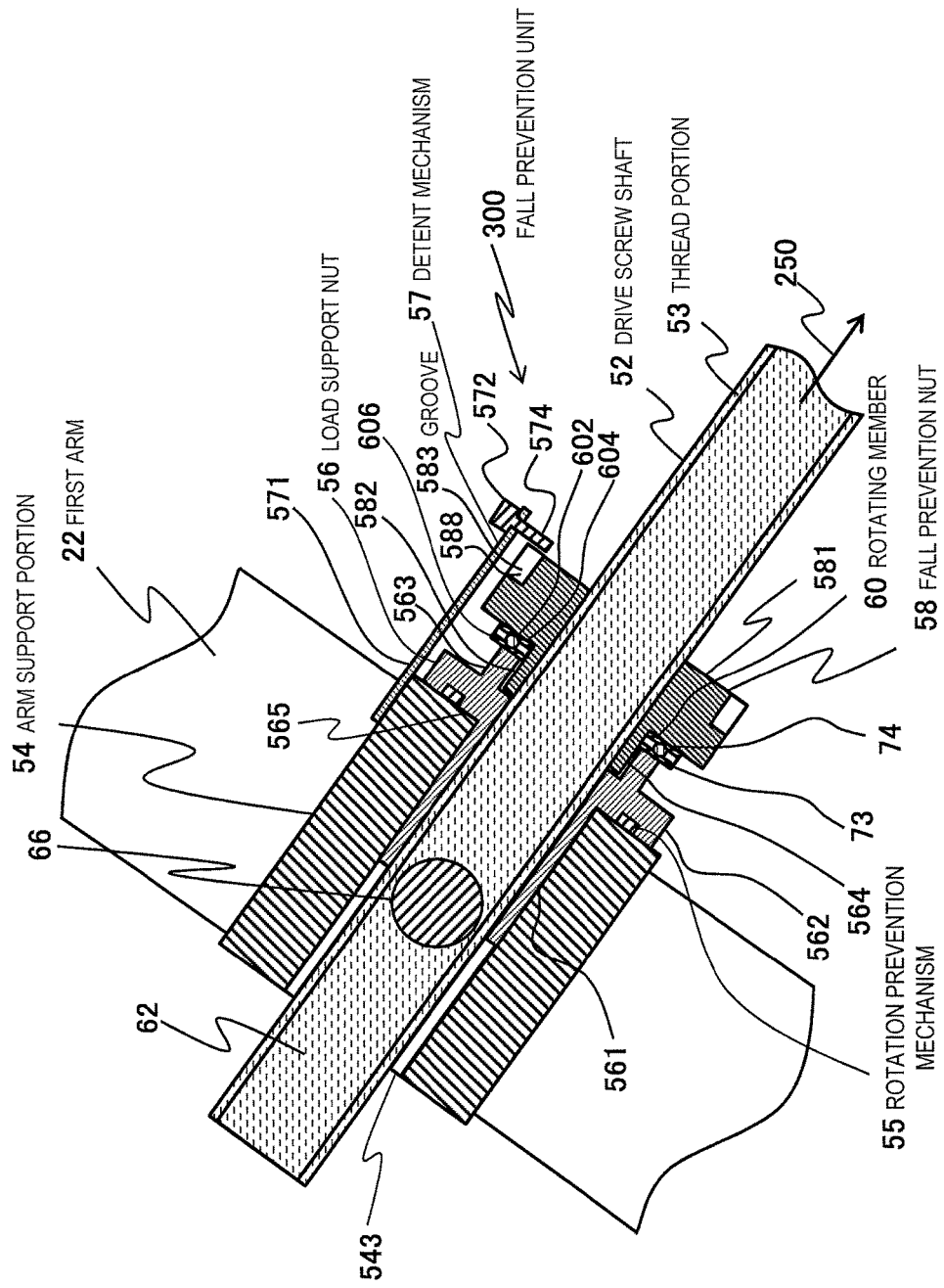
FIG. 4 is a longitudinal sectional view illustrating a state where a load support nut has fallen from the state of FIG. 3.

FIG. 4 is a longitudinal sectional view illustrating a state where the load support nut 56 has fallen from the state of FIG. 3. Since the load support nut 56 receives the load of the arms 20 that is received via the arm support portion 54, the female thread portion of the load support nut 56 threadedly engaged with the thread portion 53 that is a male thread continues the rotational driving of the drive screw shaft 52 over time, and is thereby worn out earlier than the female thread portion of the fall prevention nut 58.

Accordingly, the female thread portion of the worn-out load support nut 56 is released from the threaded engagement of the thread portion 53 of the drive screw shaft 52 at a certain time, and accordingly, the load support nut 56 falls in a downward direction together with the arm support portion 54. Here, the term "downward direction" is the direction of a gravitational direction component along the axial direction of the drive screw shaft 52, and is a direction indicated by an arrow 250. The load support nut 56 falls in the downward direction 250 along the drive screw shaft 52 with the arm support portion 54. That is, the top plate 12 falls toward the ground.

In this way, if the load support nut 56 falls in the downward direction, as illustrated in FIG. 4, the protruding portion 563 of the load support nut 56 and the rotating member 60 come into contact with each other, the end 574 of the detent 572 of the detent mechanism 57 protrudes from the groove 583 farther than an opening side of the groove 583 of the fall prevention nut 58.

Accordingly, the turning stop of the fall prevention nut 58 is released, and the fall prevention nut becomes rotatable along with the rotation of the drive screw shaft 52. In such a state, the fall prevention nut 58 receives the load from the load support nut 56, that is, the load from the top plate 12 indirectly via the rotating member 60. Since the fall prevention nut 58 is threadedly engaged with the drive screw shaft 52, and the load from the top plate 12 received, falling of the load support nut 56 is prevented. That is, when the rotating member 60 has come into contact with the load support nut 56, falling of the top plate 12 is prevented.

In this case, if a rolling friction force between the load support nut 56 and the fall prevention nut 58 is made smaller than a sliding friction force between the fall prevention nut 58 and the drive screw shaft 52, and the drive screw shaft 52 is rotated in this state, the fall prevention nut 58 slides against the rotating member 60 with this rotation and is rotated. That is, the drive screw shaft 52 is brought into an idling state together with the fall prevention nut 58 with respect to the load support nut 56 and the arm support portion 54.

Since the load support nut 56 of which the threaded engagement has been released cannot perform linear movement thereof caused by screw movement even if the drive screw shaft 52 is rotated, the lifting and lowering movement of the arms 20 is no longer performed even if the drive screw shaft 52 is driven.

Since the bed 100 for medical image scanning of the present embodiment has the above structure, the lifting and lowering of the arms 20 are not performed irrespective of whether the operator of the bed height adjustment unit 50 has driven the bed height adjustment unit 50 as described above, at the time of the falling of the load support nut 56. Therefore, the abnormality of the device in which the load support nut 56 has fallen, that is, a failure occurring in the bed height adjustment unit 50 can be recognized in an early stage at the time of the occurrence of an abnormality. Therefore, it is possible to prevent a serious accident in which the lifting and lowering movement of the bed is continued without an operator noticing that the load support nut 56 has been worn out, and thereby, the top plate 12 falls suddenly at a certain time and an object is seriously injured.

If the abnormality of the device can be recognized in an early stage, it is possible to take measures, such as interrupting scanning work or the like immediately, and performing replacement of parts. Accordingly, it is possible to prevent rapid falling of the top plate 12 to the base 1 resulting from the threaded engagement of the drive screw shaft 52 with the thread portion 53 being released due to the wearing of the female thread portion of the fall prevention nut 58 and resulting from the arm support portion 54 and the load support nut 56 falling together with the fall prevention nut 58 if the above abnormality is not noticed in an early stage. Therefore, an object's safety can be maintained.

In this way, the bed 100 for medical image scanning of the present embodiment is characterized in that the rotating member 60 is provided between the load support nut 56 and the fall prevention nut 58, the fall prevention nut 58 supports the rotating member 60 and the rotating member 60 supports the load support nut 56 in a state where the threaded engagement between the drive screw shaft 52 and the load support nut 56 is disconnected, and a rolling friction force between the load support nut 56 and the fall prevention nut 58 is smaller than the sliding friction force between the fall prevention nut 58 and the drive screw shaft 52. According to the above configuration, the embodiment of the invention can provide the medical image scanning system provided with a bed that can further improve an object's safety.

Here, as the rotating member 60, for example, a rolling bearing like a thrust bearing consisting of a ball 602 and rings 604 and 606 that sandwiches the ball 602 so as to be rotatable on its axis is used. When the rotating member 60 is constituted of a rolling bearing, such as the above-described thrust bearing, this rolling bearing may receive the load from the load support nut that has fallen in the downward direction, and the rolling friction force between the load support nut 56 and the fall prevention nut 58 may be made smaller than the sliding friction force between the fall prevention nut 58 and the drive screw shaft 52. Accordingly, the same effects as the above-described effects can also be exhibited. Additionally, the rotating member 60 may be constituted of an oil-retaining bearing in which a lubricant is impregnated in a sintered body of a metallic material. Accordingly, the same effects as the above-described effects can also be exhibited.

Additionally, the rotating member 60 may have a first member and a second member including surfaces that closely face each other and support the first member and the second member so as to be mutually rotatable; the fall prevention nut 58 may support the first member, the first member may rotatably support the second member, and the second member may support the load support nut 56, in a state where the threaded engagement between the drive screw shaft 52 and the load support nut 56 is disconnected; and a frictional force between the first member and the second member may be smaller than a sliding friction force between the fall prevention nut 58 and the drive screw shaft 52. In this case, for example, metallic materials with low frictional coefficients can be respectively adopted for the first member and the second member. Accordingly, the same effects as the above-described effects can also be exhibited.

Additionally in the above-described configuration, the rotating member 60 may be configured such that a low friction material including molybdenum may be carried between the first member and the second member. Since this molybdenum has the low frictional coefficient, it is suitable for the rotating member. Specifically, the rotating member may be formed by coating molybdenum between the first member and the second member. Accordingly, the same effects as the above-described effects can also be exhibited.

Additionally in the above-described configuration, the rotating member 60 may be configured such that a lubricant may be injected between the first member and the second member. Accordingly, the same effects as the above-described effects can also be exhibited. Additionally, according to this configuration, the economical rotating member 60 can be provided because it is not necessary to provide a low-friction lubricating material as the above embodiment.

Additionally, the shape of the protruding portion 563 of the load support nut 56 only has to be able to transmit the load of the arm 20 to the fall prevention nut 58 via the rotating member 60, and may be constituted of a plurality of pins that are intermittently arranged in the circumferential direction.

Figure 5:
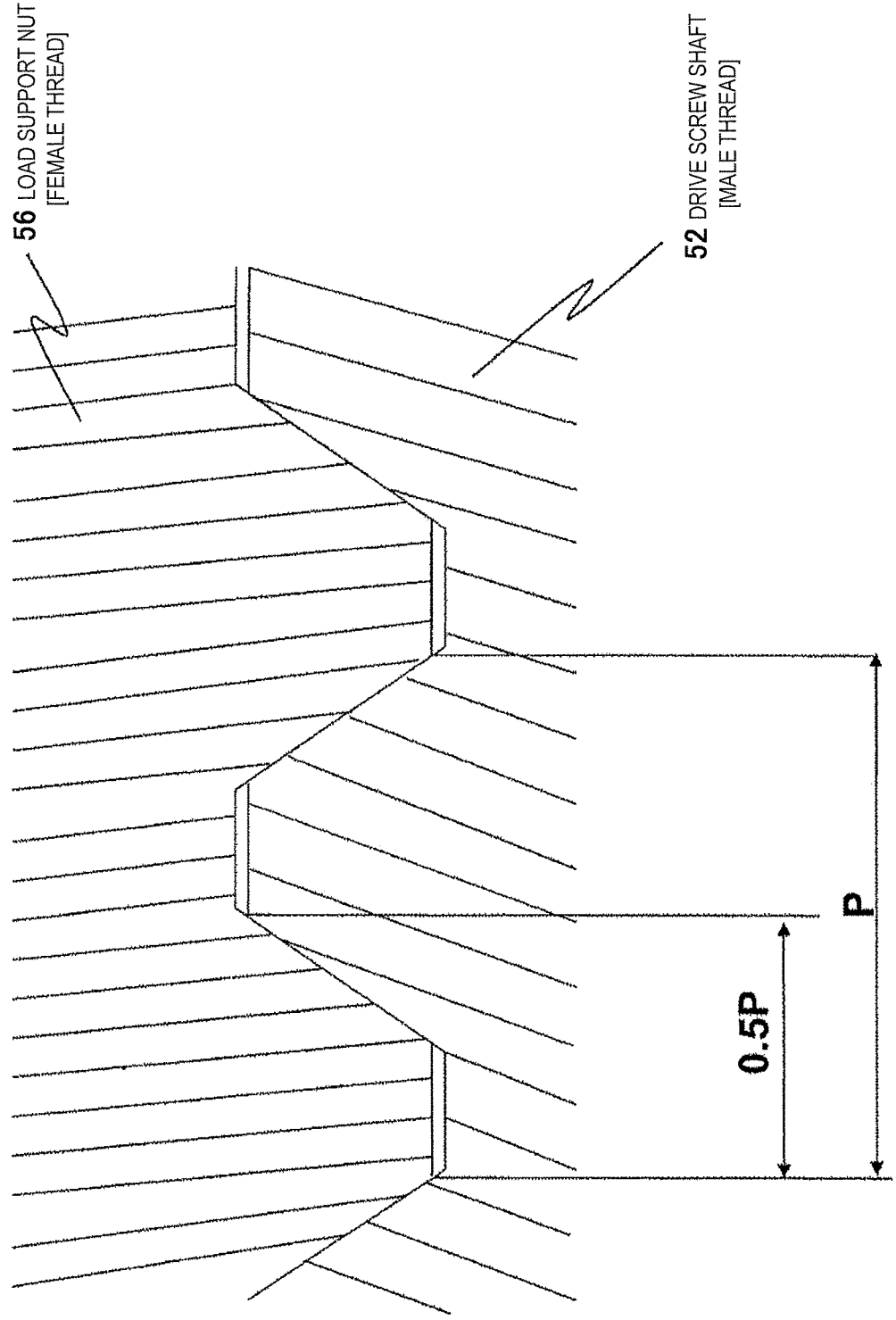
FIG. 5 is an enlarged longitudinal sectional view illustrating a place where the load support nut and a drive screw shaft are threadedly engaged with each other.
Figure 6:
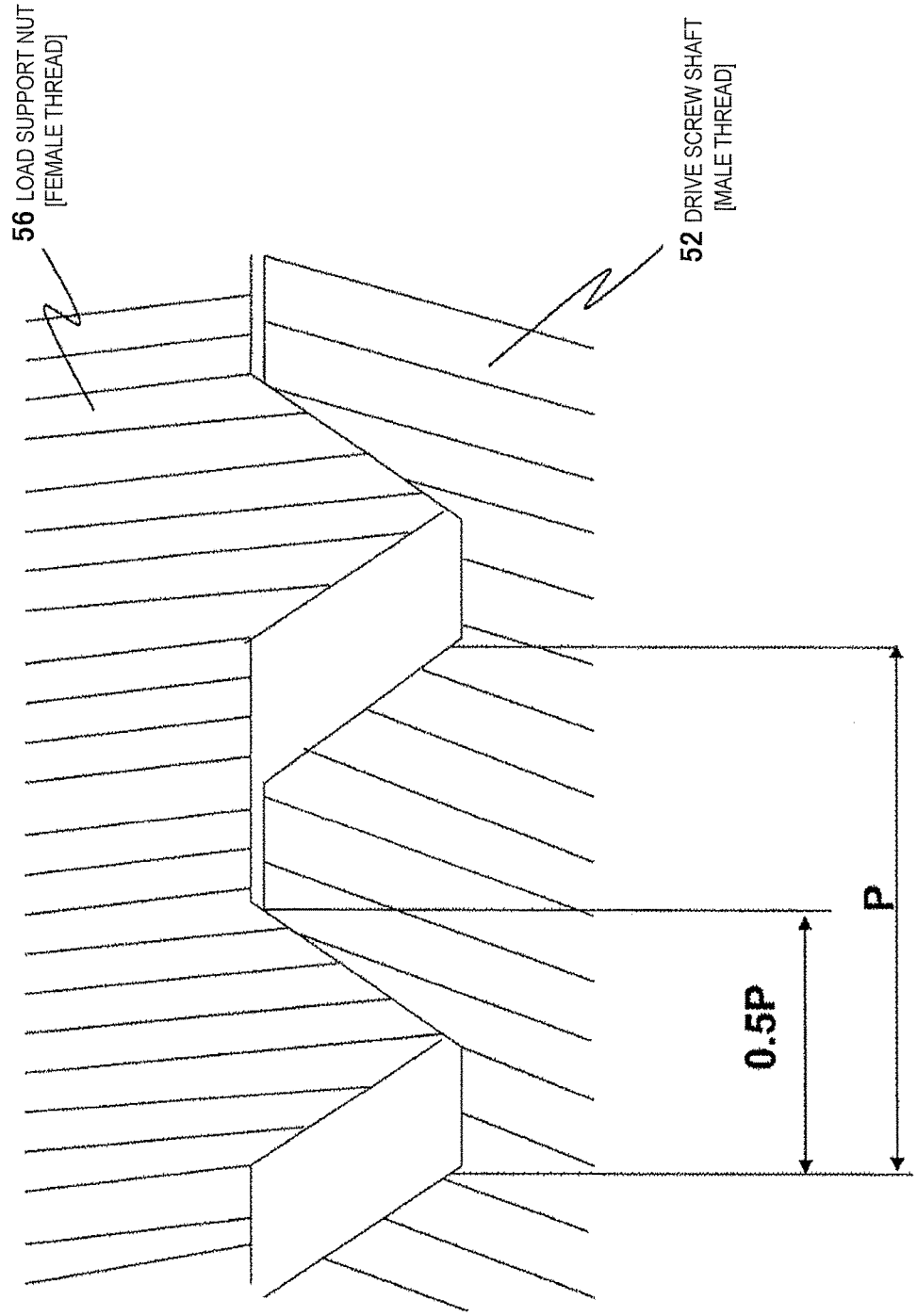
FIG. 6 is a longitudinal sectional view illustrating a state where the load support nut has worn from the state of FIG. 5.

FIGS. 5 and 6 are enlarged longitudinal sectional views of a place where the load support nut 56 and the drive screw shaft 52 are threadedly engaged with each other, and P in this drawing is screw pitch. In addition, FIG. 5 illustrates a state before the load support nut 56 is worn out, and FIG. 6 illustrates a state where the load support nut 56 has been worn out.

When the wear of the load support nut 56 proceeds and the wear of 0.5 P has occurred, the ridge of a female thread of the load support nut 56 disappears completely, and the load support nut 56 falls. Thus, if the distance D between the load support nut 56 and the rotating member 60 is made equal to or more than 0.5 P, the load support nut 56 can be used up until the ridge of the female thread of the load support nut 56 disappears completely. For example, when the screw pitch is 6 mm, the distance D between the load support nut 56 and the rotating member 60 is made equal to or more than 3 mm.

Additionally, by making the distance D between the load support nut 56 and the rotating member 60 a value of 15 mm or less, shock to an object when the load support nut 56 falls can be reduced.

Moreover, in the bed 100 for medical image scanning of the present embodiment, the drive screw shaft 52 inclines with respect to a vertical axis of the top plate 12. Thus, the vertical fall distance of the top plate 12 can be smaller than the distance D, and shock to an object can be further reduced.

Figure 7:
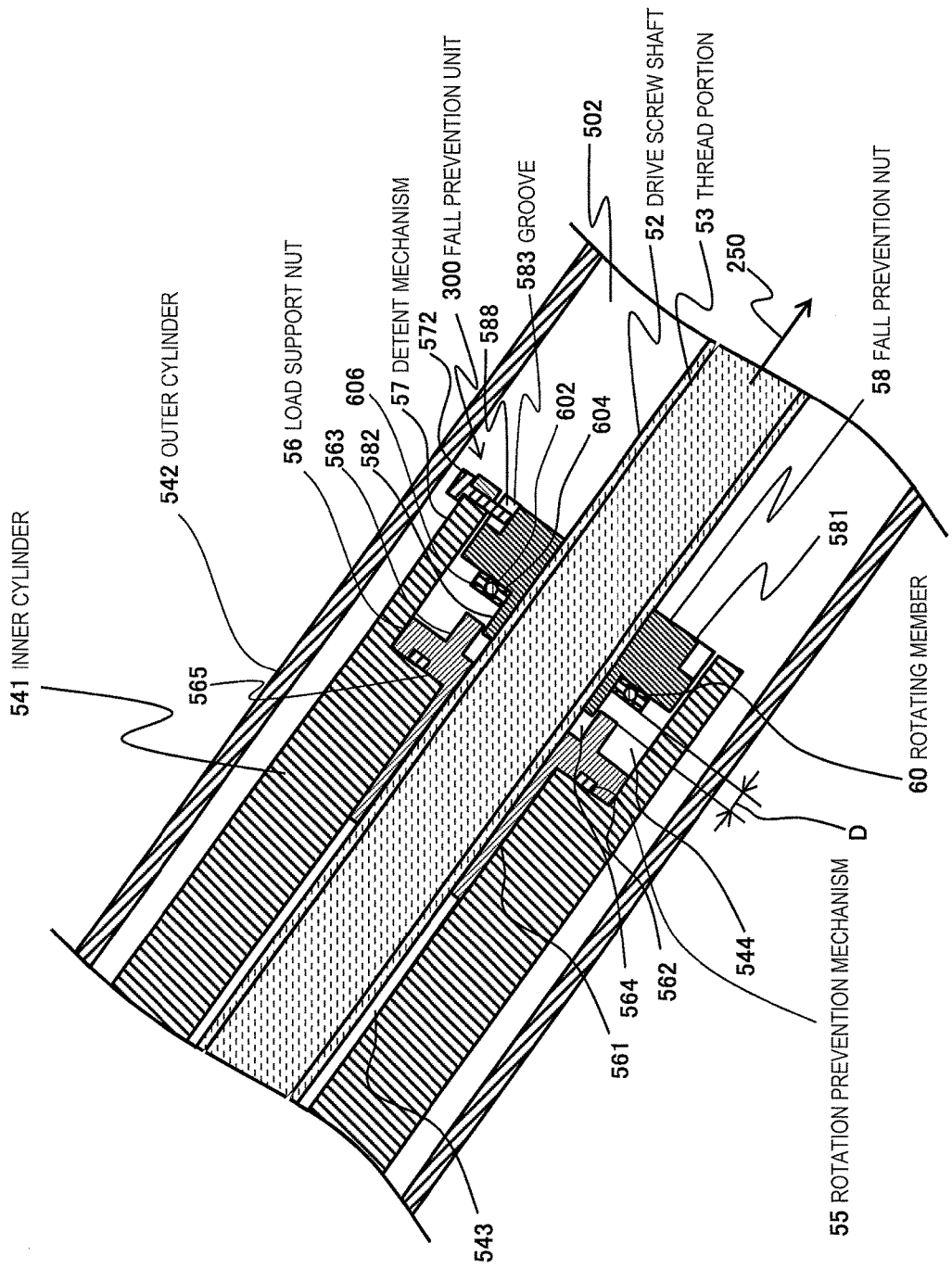
FIG. 7 is a longitudinal sectional view illustrating a detailed configuration of a fall prevention unit of the medical image scanning system provided with the bed on which an object is placed, in another embodiment of the invention.

FIG. 7 is a longitudinal sectional view illustrating a detailed configuration of a fall prevention unit of the medical image scanning system provided with the bed on which an object is placed, in another embodiment of the invention. The bed 100 for medical image scanning of the present embodiment may be a bed height adjustment unit 502 configured (referred to as a cylinder configuration) such that the load support nut 56 is fitted into the opening 543 of an inner cylinder 541, the support portion 562 and the protruding portion 563 of the load support nut 56, the rotating member 60, and the fall prevention nut 58 is provided within the opening 544 of the inner cylinder 541, the detent mechanism 57 is formed integrally with the inner cylinder 541 (hereinafter, these are generically referred to as screw mechanism portions), the load support nut 56 and the fall prevention nut 58 are threadedly engaged with the drive screw shaft 52, and the screw mechanism portions are arranged within the outer cylinder 542.

By adopting the above configuration, all these screw mechanism portions are provided within the outer cylinder 542, that is, the outer cylinder 542 covers these screw mechanism portions. Thus, dust or dirt can be prevented from entering the thread portion from the outside.

Additionally, since the detent mechanism 57 is integrated with the inner cylinder 541, the number of parts can be reduced, and the strength of the detent mechanism 57 can be improved compared to a case where the detent mechanism 57 and the arm support portion 54 are separately provided as in the example illustrated in FIG. 3 and FIG. 4. Therefore, a reliable medical image scanning system can be provided.

Embodiment 2

Figure 8:
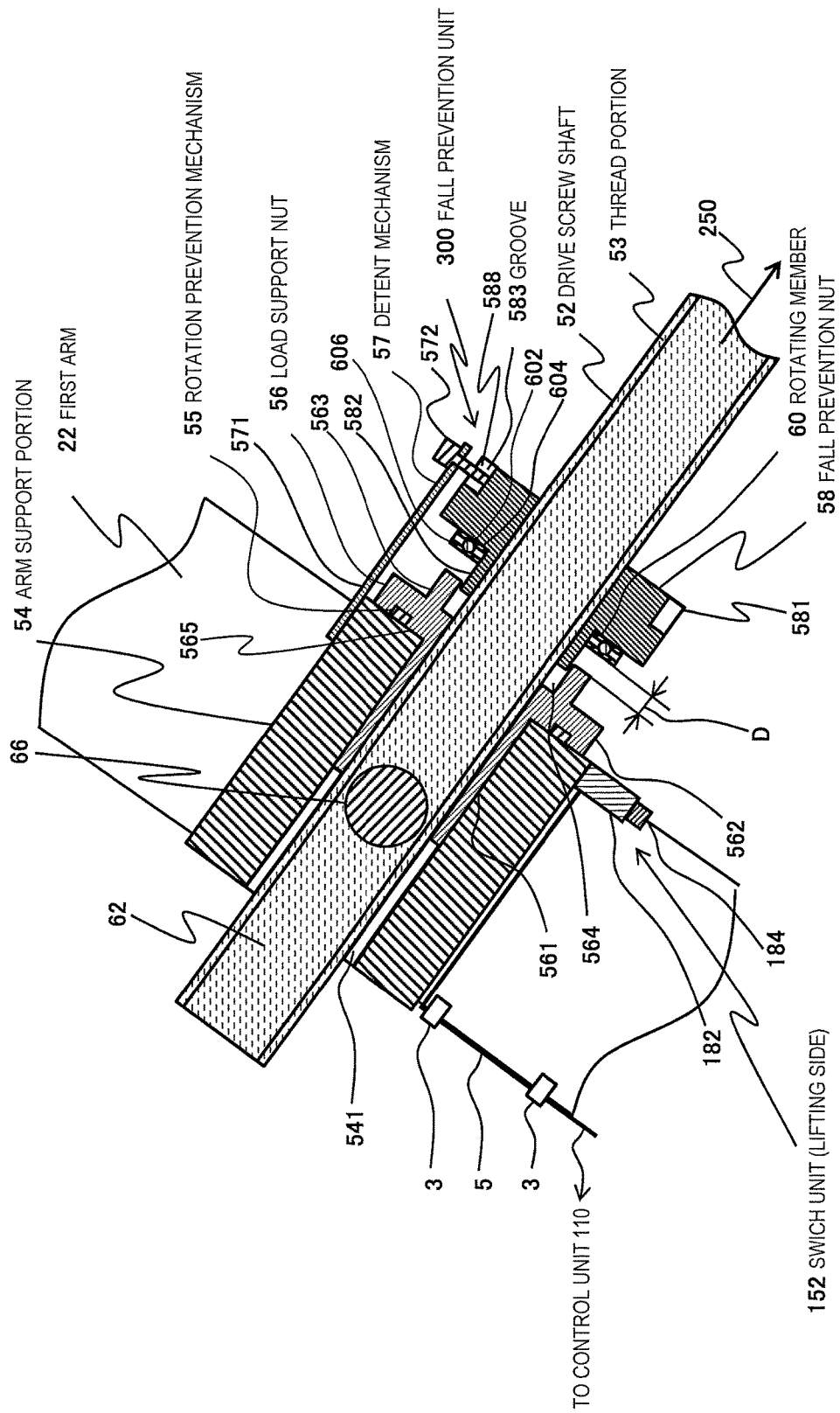
FIG. 8 is a longitudinal sectional view illustrating a detailed configuration of a fall prevention unit of the medical image scanning system provided with the bed on which an object is placed, in still another embodiment of the invention.
Figure 9:
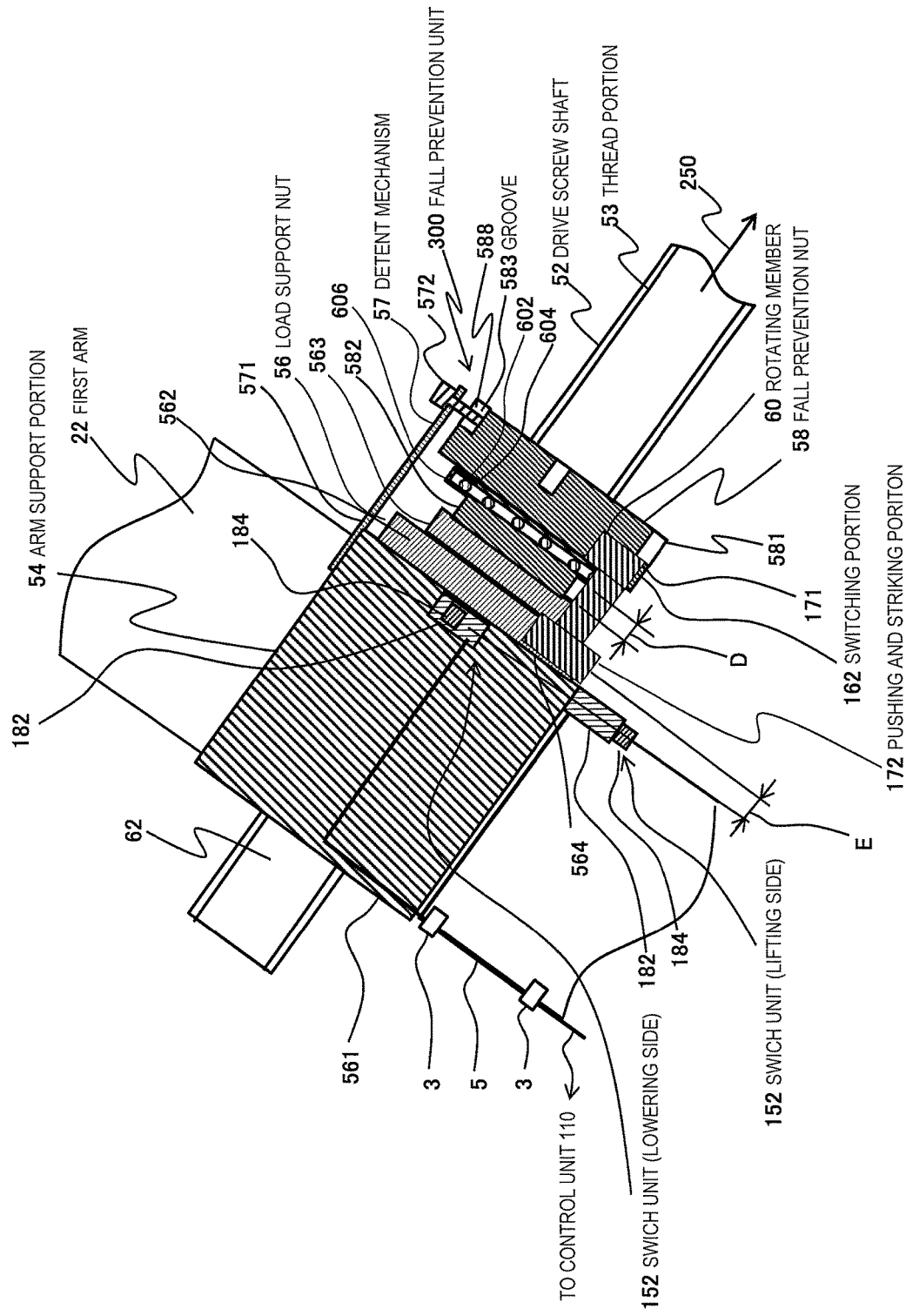
FIG. 9 is a side view illustrating a detailed configuration of the fall prevention unit in the state of FIG. 8.
Figure 10:
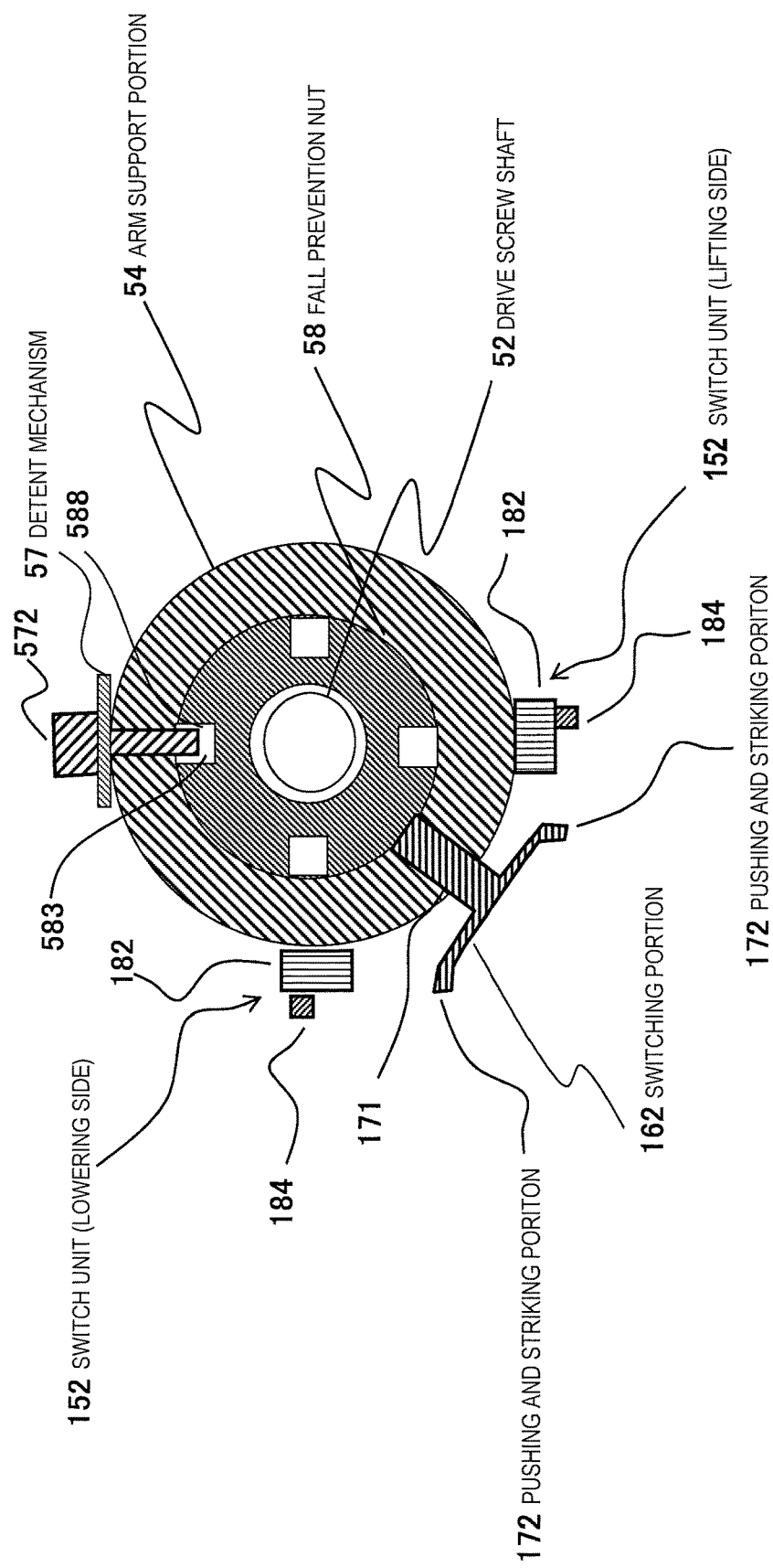
FIG. 10 is a perspective view illustrating the details of the fall prevention unit in the state of FIG. 8.

FIG. 8 is a longitudinal sectional view illustrating a detailed configuration of a fall prevention unit of the medical image scanning system provided with the bed on which an object is placed, in still another embodiment of the invention. FIG. 9 is a side view illustrating a detailed configuration of the fall prevention unit in the state of FIG. 8. FIG. 10 is a perspective view illustrating the details of the fall prevention unit in the state of FIG. 8. This embodiment is characterized by including a switch unit 152 that generates a signal for being sent to the control unit 110 when the threaded engagement between the drive screw shaft 52 and the load support nut 56 is disconnected and the load support nut 56 has fallen. Hereinafter, detailed description will be made.

The bed 100 for medical image scanning of the present embodiment is configured such that the arm support portion 54 is provided with a two-point switch unit 152 in which signals are sent to the control unit 110 by switch depression, and the fall prevention nut 58 is provided with a switching portion 162 that is an actuating member that performs switch depression by contacting the switch unit 152 by the rotation of the fall prevention nut 58 synchronized with the rotation of the drive screw shaft 52.

Each switch unit 152 is constituted of a switch button portion 184 and a switch holder 182 that holds this switch button portion 184 and is fixed and connected to the arm support portion 54. As the two-point switch unit 152, there are two types a switch unit 152 for performing switch depression at the time of the rotation of the drive screw shaft 52 in a lifting direction, and a switch unit 152 for performing switch depression at the time of the rotation thereof in a lowering direction. The fixed positions of the switch units 152 are on the same circumference with the central axis of the drive screw shaft 52 as a center, and a space equal to or greater than the width of the switching portion 162 has only to be provided so as not to interfere with the switching portion 162 when the relative positions of two points have fallen together with the load support nut 56.

For example, the switch unit 152 for performing switch depression at the time of the rotation in an lifting direction is provided at the position of 180° with respect to the detent mechanism 57 with the central axis of the drive screw shaft 52 as a center as illustrated, and the switch unit 152 for performing switch depression at the time of the rotation in a lowering direction is provided at the position of 90° with respect to the switch unit 152 on the lifting side. The communication unit 5 through which a signal is transmitted to the control unit 110 is connected to the switch holder 182 of the switch unit 152, and a signal generated on the basis of the switch depression of the switch button portion 184 by pushing and striking is transmitted to the control unit 110 via the communication unit 5. The communication unit 5 is attached and fixed to the first arm 22, for example, by fixing means 3. In this way, the switch unit 152 is constituted as an opening/closing portion that electrically performs an opening/closing operation.

The switching portion 162 consists of a pushing and striking portion 172 from which an end protrudes, and a fixed and connected portion 171 that is fixed and connected to the fall prevention nut 58. The fixed position of the switching portion 162 has only to be provided at a position where the distance E between the pushing and striking portion 172 and the switch button portion 184 in the axial direction of the drive screw shaft 52 becomes equal to the distance D between facing surfaces of the load support nut 56 and the rotating member 60, a position where the pushing and striking portion 172 is present on the same circumference as the two-point switch button portion 184, and a position between two points of the switch button portion 184 where the switching portion 162 and the switch unit 152 do not come into contact with each other when the load support nut 56 has fallen. The pushing and striking portion 172 is formed so as to come into contact with and push and strike the switch button portion 184 at a certain rotation time, on the basis of the rotation of the fall prevention nut 58.

Figure 11:
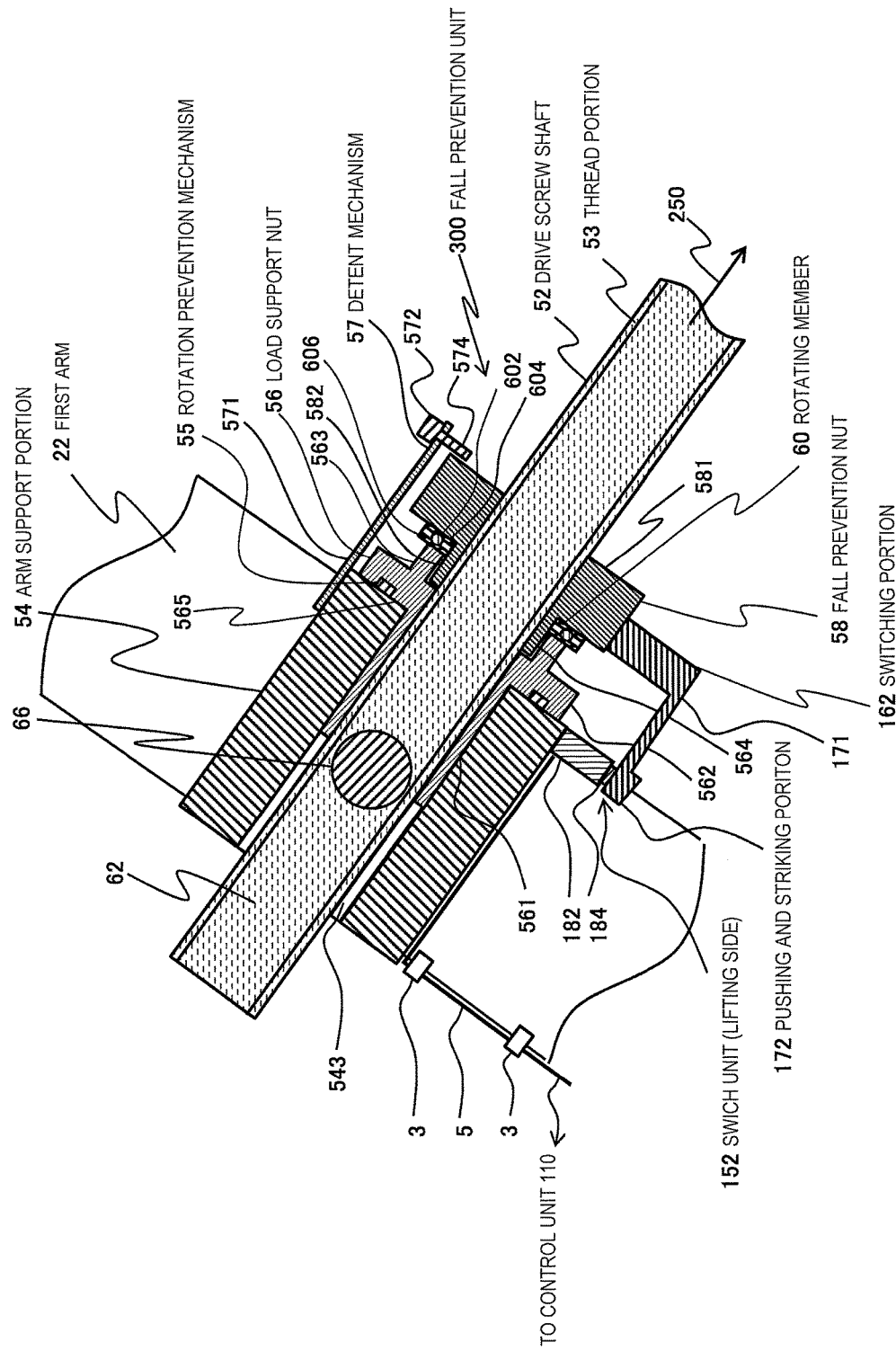
FIG. 11 is a longitudinal sectional view illustrating a state where the load support nut has fallen from the state of FIG. 6, the fall prevention nut has been rotated in a lifting direction, and a switch has been depressed.
Figure 12:
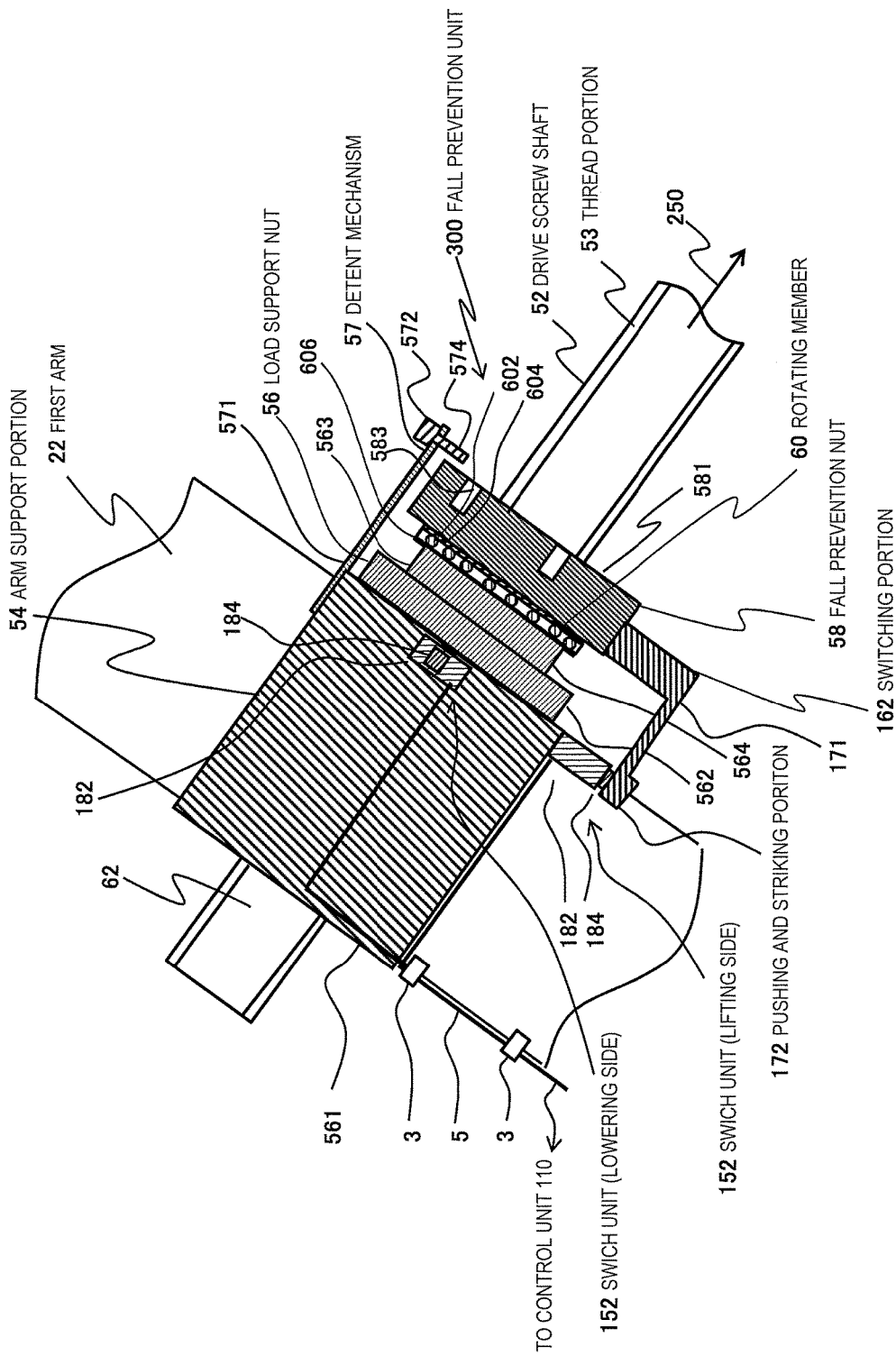
FIG. 12 is a side view illustrating a detailed configuration of the fall prevention unit in the state of FIG. 10.
Figure 13:
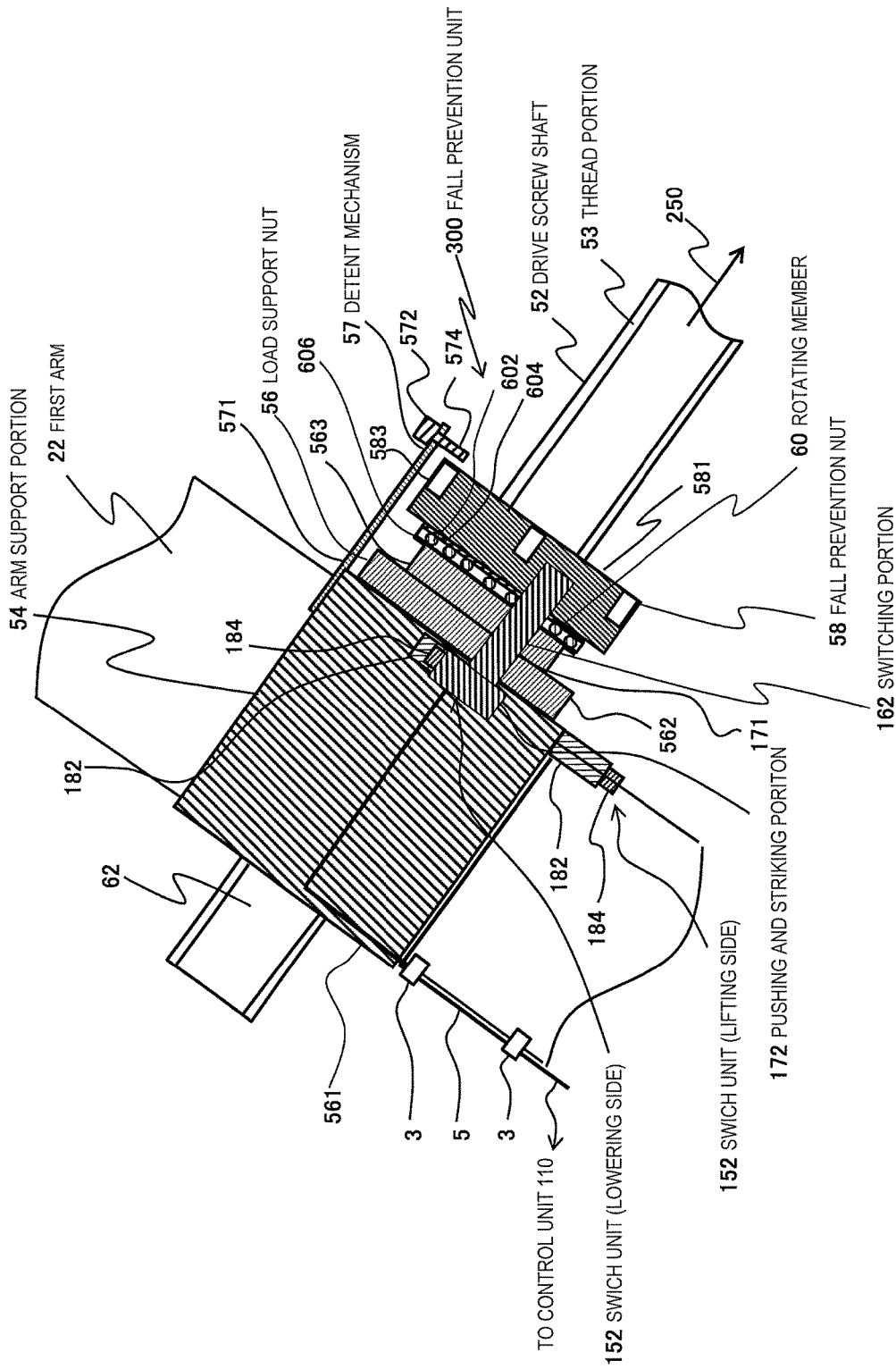
FIG. 13 is a side view illustrating a state where the load support nut has fallen from the state of FIG. 9, the fall prevention nut has been rotated in a lowering direction, and the switch has been depressed.

FIG. 11 is a longitudinal sectional view illustrating a state where the load support nut 56 has fallen from the state of FIG. 8, the fall prevention nut 58 has been rotated in the lifting direction, and a switch has been depressed. FIG. 12 is a side view in the state of FIG. 11. FIG. 13 is a side view illustrating a state where the load support nut 56 has fallen from the state of FIG. 8, the fall prevention nut 58 has been rotated in the lowering direction, and the switch has been depressed. By adopting the above configuration, as the load support nut 56 falls together with the switch unit 152 and comes into contact with the rotating member 60 as described above, the falling of the bed 100 for medical image scanning of the present embodiment stops. In this case, the two switch units 152 stop at a position where the switch units sandwich the switching portion 162 without coming into contact with the switching portion. Additionally, the switch button portion 184 is located at a position on the same circumference as the pushing and striking portion 172 with the central axis of the drive screw shaft 52 as a center. Therefore, as the fall prevention nut 58 of which the turning stop has been released is rotated in the elevating direction or lowering direction together with the drive screw shaft 52, the switch button portion 184 in the elevating direction or lowering direction is switch-depressed by the pushing and striking portion 172 as illustrates at a certain time, a signal is generated on the basis of this, and the signal is sent to the control unit 110 via the communication unit 5.

Since the control unit 110 can display, for example, a display showing that an abnormality has occurred in the device by using this sent signal, on the display section 132 of the output unit 130, the abnormality of the device that the load support nut 56 has fallen, that is, a failure has occurred in the bed height adjustment unit 50 can be recognized in an early stage similar to the above-described embodiment, and an object's safety can be maintained. Therefore, similar to the above-described embodiment, it is possible to prevent a serious accident in which the lifting and lowering movement of the bed is continued without an operator noticing that the load support nut 56 has been worn out, and thereby, the top plate 12 falls suddenly at a certain time and an object is seriously injured.

In this way, in the bed 100 for medical image scanning of the present embodiment, the switch unit 152 includes the actuating member, and the opening/closing portion that electrically performs an opening/closing operation; this opening/closing portion is provided so as to move together with the load support nut 56 and the actuating member is provided so as to move together with the fall prevention nut 58; and the actuating member actuates the opening/closing portion on the basis of a change in the distance between the load support nut 56 and the fall prevention nut 58 resulting from the threaded engagement between the drive screw shaft 52 and the load support nut 56 being disconnected, and the load support nut 56 has fallen, and a signal for being sent to the control unit 110 is generated by the opening/closing portion.

Here, in the present embodiment, the fall prevention nut 58 releases the turning stop at the time of the falling of the load support nut 56 as described above. Therefore, when the fall prevention nut 58 is provided with the switch unit 152 and when the communication unit 5 connected to the switch unit 152 is a wire, the wire has rotated along with the rotation of the fall prevention nut 58 of which the turning stop has been released. As a result, the wire is entangled in the drive screw shaft 52. Due to this, there is a concern that the communication unit 5 may cause disconnection or poor communication, and signal communication may not reliably performed.

Therefore, when the communication unit 5 that is a wire is used, it is preferable to provide the switch unit 152 in the load support nut 56 of which the turning stop has been performed, and to provide the switching portion 162 in the fall prevention nut 58 correspondingly. By adopting such a configuration, there is no influence caused by the rotation of the drive screw shaft 52 or the fall prevention nut 58 of which the turning stop has been released, and a concern that signal communication may not be reliably performed also disappears. When the communication unit 5 is constituted in a wireless manner, a problem in which the wire is entangled as described above does not occur. Thus, the switch unit 152 and the switching portion 162 may be provided in either the load support nut 56 or the fall prevention nut 58.

In this way, with respect to the embodiment illustrated in FIGS. 8 to 13, one of the arm support portion 54 and the fall prevention nut 58 may be provided with the switch unit 152 from which signals are sent to the control unit 110 by switch depression, and the other hand may be provided with the switching portion 162 that performs switch depression by contacting the switch unit 152 by the rotation of the fall prevention nut 58 synchronized with the rotation of the drive screw shaft 52.

Figure 14:
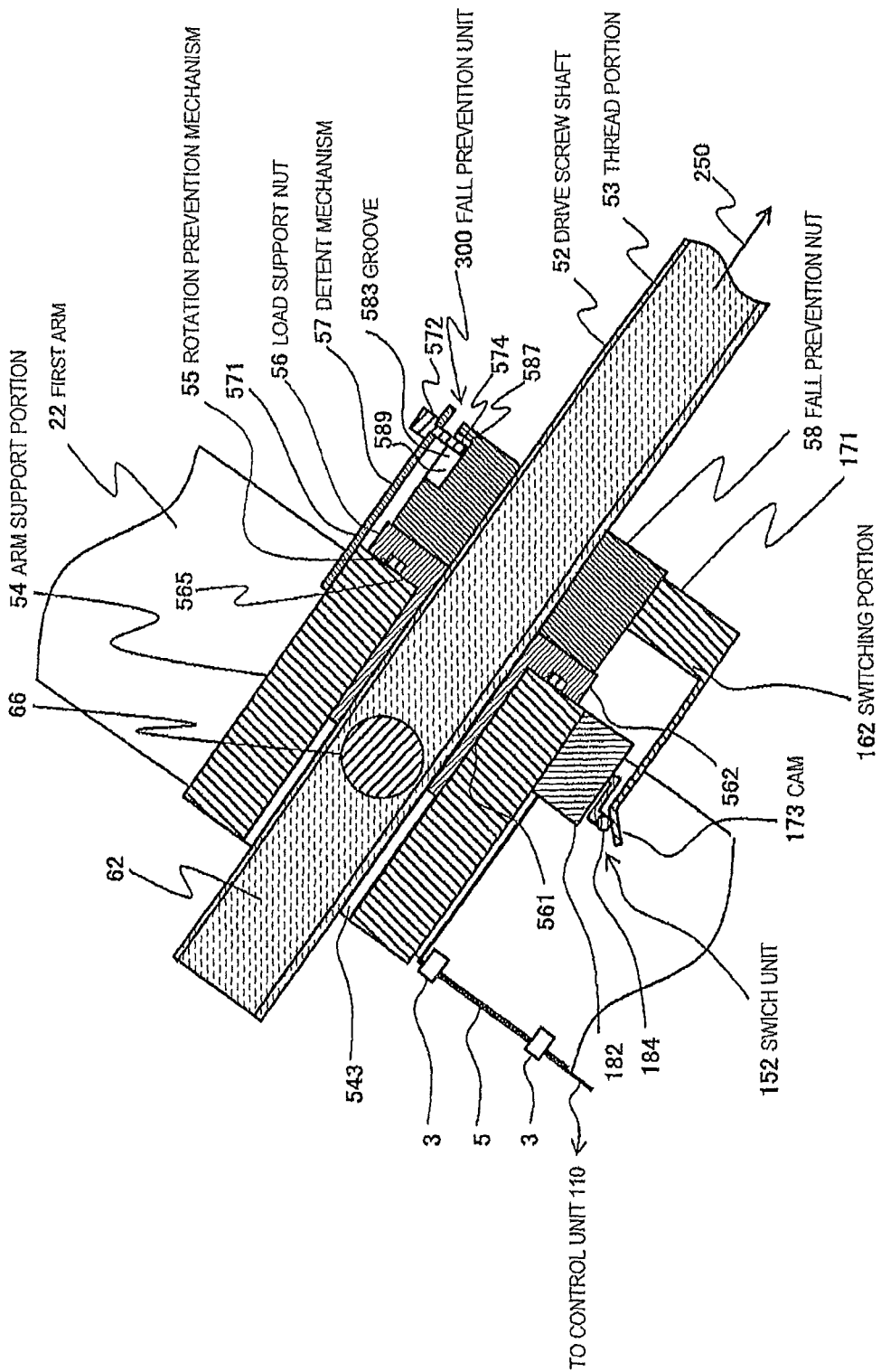
FIG. 14 is a longitudinal sectional view illustrating a detailed configuration of a fall prevention unit of the medical image scanning system provided with the bed on which an object is placed, in still another embodiment of the invention, and illustrating a state where the load support nut has fallen and the switch has been depressed.

FIG. 14 is a longitudinal sectional view illustrating a detailed configuration of a fall prevention unit of the medical image scanning system provided with the bed on which an object is placed, in still another embodiment of the invention, and illustrating a state where the load support nut has fallen and the switch has been depressed. In this embodiment, the rotating member 60 is not provided between the load support nut 56 and the fall prevention nut 58, and the load support nut 56 comes into contact with the fall prevention nut 58 directly at the time of falling.

Additionally, in this embodiment, a plurality of grooves 584 formed in the direction of the central axis of the lateral portion 588 are intermittently formed in the circumferential direction in the head 581 of the fall prevention nut 58, and the end 574 of the detent 572 is locked to the lateral portion 589 in one groove 584, and is movable in the direction of the central axis.

Accordingly, even if the fall prevention nut 58 receives the rotary power based on the rotation of the drive screw shaft 52, the fall prevention nut cannot be rotated by the end 574 of the detent 572 being locked to the lateral portion 589. That is, the fall prevention nut 58 is brought into a state where the turning thereof is stopped by the rotating member 57, similar to the load support nut 56.

Additionally, a side surface 587 is formed on the lower side in the direction of the central axis, that is, on the end 63 side of the drive screw shaft 52 in the groove 584 of the fall prevention nut 58, and the end 574 of the detent 572 that has moved due to the falling of the load support nut 56 is locked by the side surface 587. Therefore, the turning stop of the fall prevention nut 58 is not released even if the load support nut 56 falls.

Additionally, the switching portion 162 and the switch unit 152 are provided at corresponding positions, respectively. By virtue of the above configuration, when the load support nut 56 falls and comes into contact with the fall prevention nut 58, a cam 173 formed at a protruding end of the switching portion 162 comes into contact with the switch button portion 184, the switch button portion 184 is switch-depressed, a signal is generated on the basis of this depression, and the signal is sent to the control unit 110 via the communication unit 5.

By virtue of such a configuration, the same effects as the above-described embodiment can also be exhibited. Additionally, in this embodiment, releasing the turning stop of the fall prevention nut 58 by the detent mechanism 57 is not required, and switch depression is rapidly performed due to the falling of the load support nut 56. Thus, compared to an example in which switch depression is performed after the turning stop of the fall prevention nut 58 is released and the fall prevention nut is rotated, a signal can be rapidly generated, and an abnormality can be rapidly determined. Additionally, since the rotating member 60 is not required, an economical medical image scanning system resulting from the reduction of the number of parts can be provided.

In addition, the switching portion 162 and the switch unit 152 may be provided in places other than the illustrated ones as long as the space between the load support nut 56 and the fall prevention nuts 58 can be secured to some extent. For example, when the cylinder configuration illustrated in FIG. 4 is applied, the cylinder configuration may be provided inside the opening 144.

Figure 15:
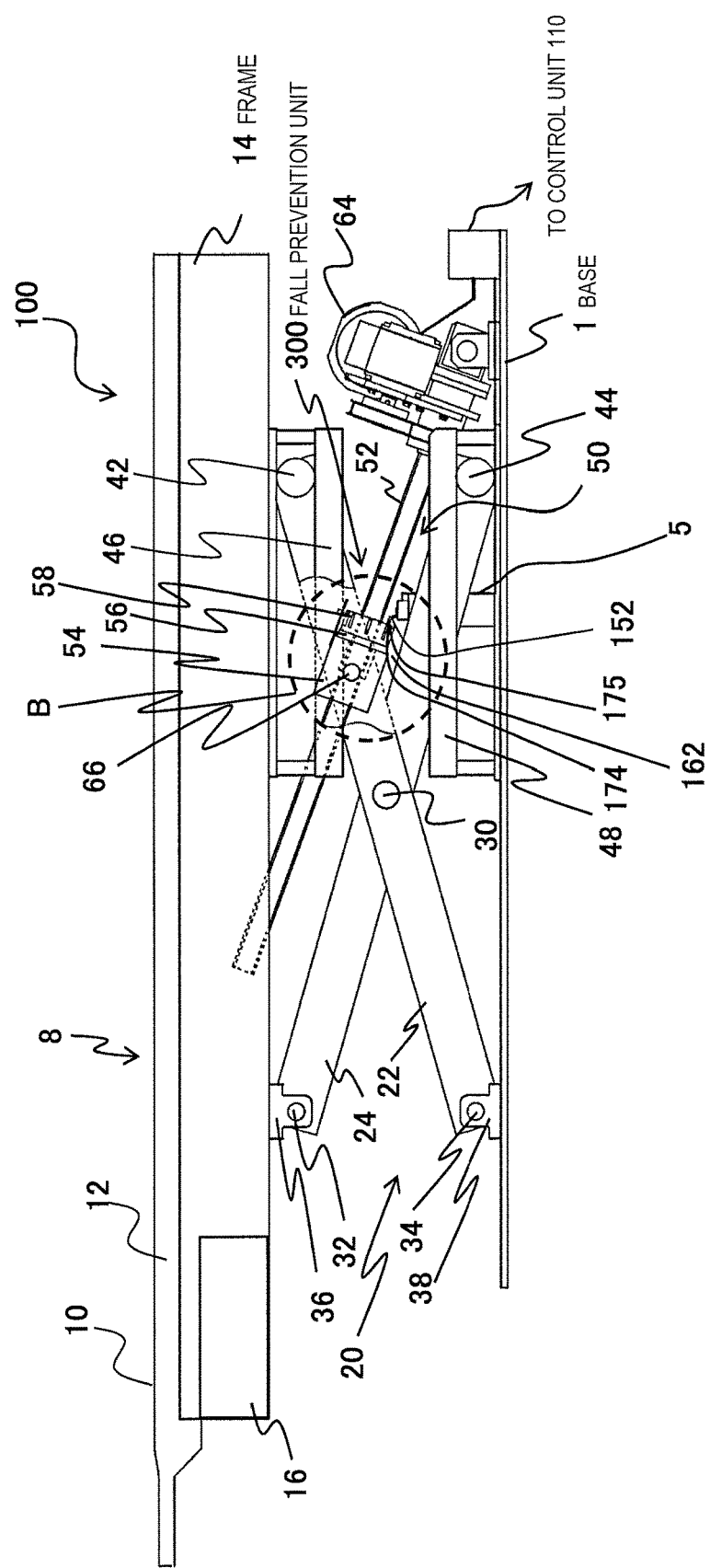
FIG. 15 is a schematic view illustrating an overall configuration of a bed provided in the medical image scanning system in still another embodiment of the invention.
Figure 16:
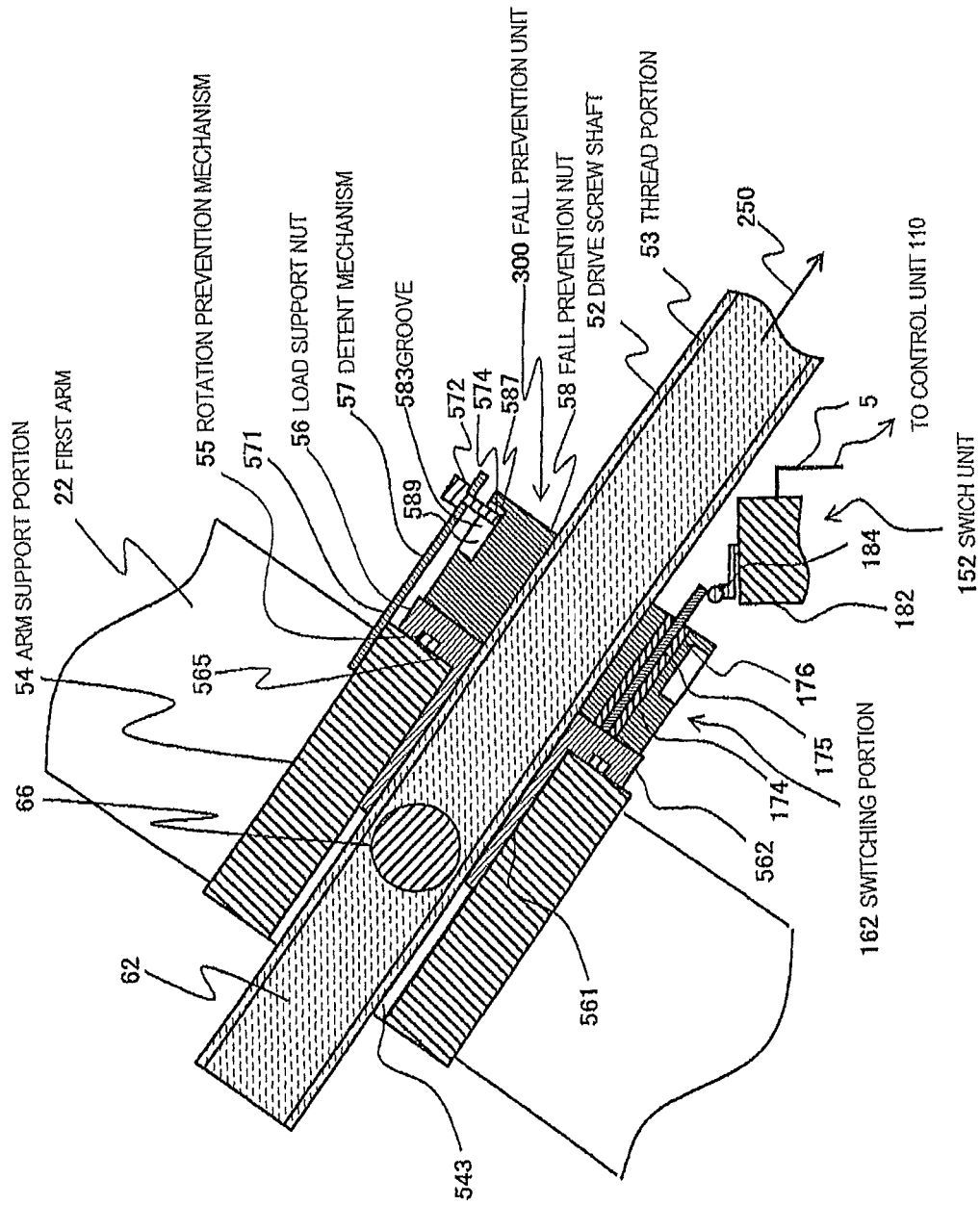
FIG. 16 is a longitudinal sectional view illustrating a detailed configuration of a fall prevention unit in FIG. 13.

FIG. 15 is a schematic view illustrating an overall configuration of a bed provided in the medical image scanning system in still another embodiment of the invention. Additionally, FIG. 16 is a longitudinal sectional view illustrating a detailed configuration of a fall prevention unit in FIG. 15. FIG. 16 illustrates a view of an enlarged portion of a region B enclosed by a dashed line illustrated in FIG. 15. In this embodiment, a hole 176 is formed in the direction of the drive screw shaft in the fall prevention nut 58, and an elastic member 175, such as rubber, and a sliding member 174, such as a pin, are arranged in the hole 176. Additionally, the switch holder 182 is provided such that the switching portion 162 is connected to the base 1.

In the bed 100 for medical image scanning that is the above configuration, when the load support nut 56 has fallen, the load support nut 56 pushes the pin 174, and thereby, the pin 174 slides against the rubber 175 and protrudes from a lower surface of the fall prevention nut 58. Then, if the top plate 12 is lowered to a lowest position, the pin 174 that has protruded from the lower surface of the fall prevention nut 58 performs switch depression of the switch button portion 184 of the switch unit 152, and thereby, a signal is generated on the basis of this depression, and a signal is sent to the control unit 110 via the communication unit 5.

By virtue of such a configuration, the same effects as the above-described embodiment can also be exhibited. Additionally, in this embodiment, when the load support nut 56 has fallen, a signal caused by switch depression is sent to the control unit 110 after the top plate 12 is lowered to the lowest position, that is, after the lifting and lowering work of the bed is completed.

Then, when the control unit 110 has received the signal, the control unit determines that work is completed or scanning is completed, and operates to rapidly stop the drive unit 65 simultaneously with the reception of the signal. Accordingly, coping with an abnormality can be rapidly and safely performed after the completion of work or the completion of scanning. Additionally, since the rotating member 60 is not required, an economical medical image scanning system resulting from the reduction of the number of parts can be provided.

Figure 17:
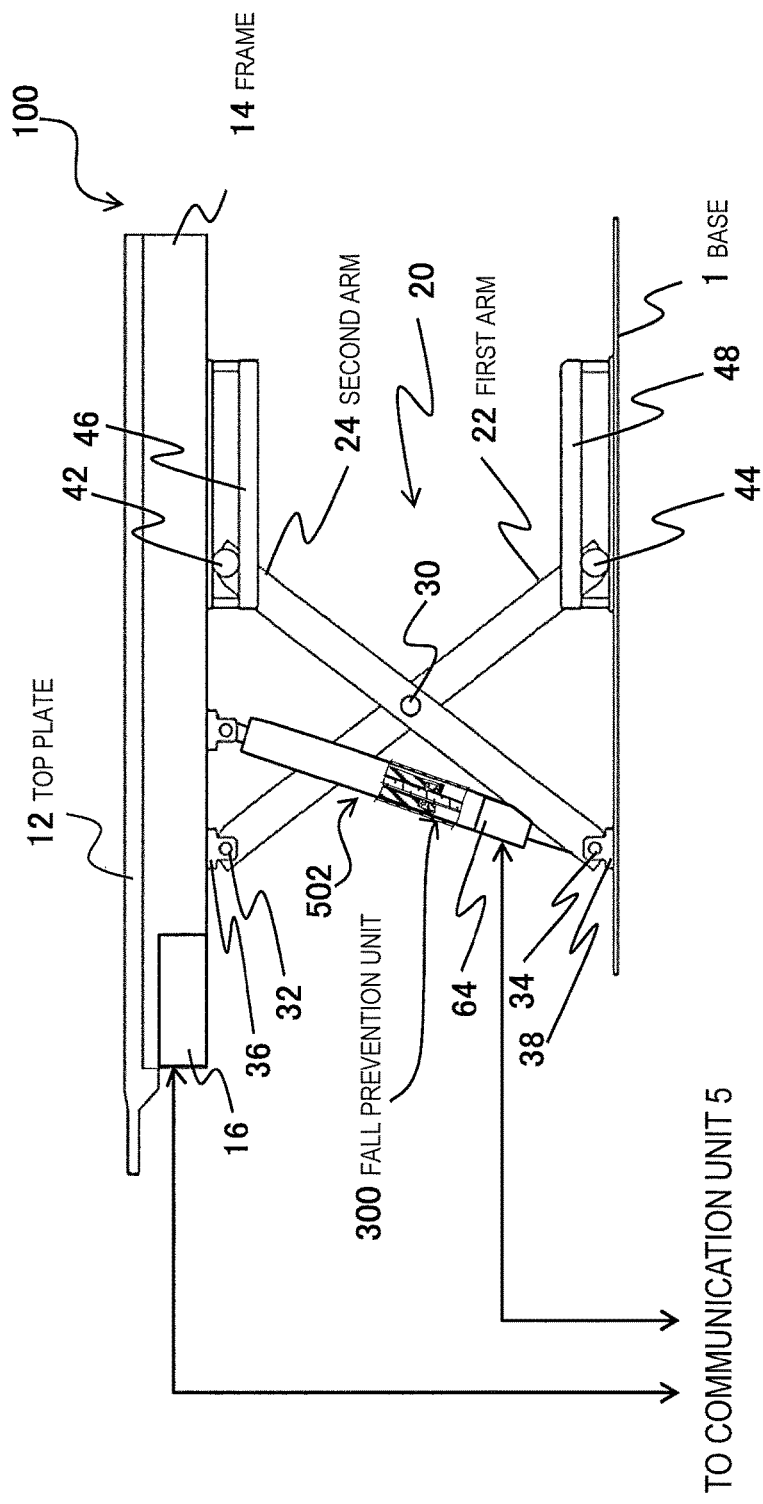
FIG. 17 is a schematic view illustrating an overall configuration of a bed provided in the medical image scanning system in still another embodiment of the invention.

FIG. 17 is a schematic view illustrating an overall configuration of a bed provided in the medical image scanning system in still another embodiment of the invention. The bed 100 for medical image scanning of this embodiment is an example in which the bed height adjustment unit 502 is driven with the power of an electric cylinder mechanism. In the electric cylinder mechanism, for example, both ends are rotatably fixed via a rotating shaft and a bearing, similar to the connection of the arms 20 with the base 1 or the frame 14 as illustrated. The drive screw shaft 52 and the screw mechanism portions are arranged within a cylinder.

The lifting and lowering of the top plate 12 is performed depending on the lifting and lowering of a cylinder (not illustrated) of an electric cylinder mechanism. The above-described fall prevention unit 300 can be applied to this electric cylinder mechanism. In the fall prevention unit 300 used in this embodiment, the same structure as the structure illustrated in FIG. 4 can be applied. The lifting and lowering of the cylinder of the electric cylinder are performed by electric driving using the drive unit 64 as a power source. The driving of the drive unit 64 is controlled by the control unit 110 via the communication unit 5.

By virtue of such a configuration, the same effects as the above-described effects can also be exhibited. Additionally, in this embodiment, the drive screw shaft 52 is arranged within the cylinder as illustrated in the drawings. Therefore, for example, when the frame 14 accompanied by the top plate 12 is lowered to the lowest position, the maximum-permissible lifting and lowering heights of the bed 100 for medical image scanning can be prevented from being hindered due to, for example, any interference of the end 62 of the drive screw shaft 52 with the frame 14. Additionally, since the drive screw shaft 52 is not exposed to the outside, entering of dust or dirt from the outside can be prevented.

Figure 18:
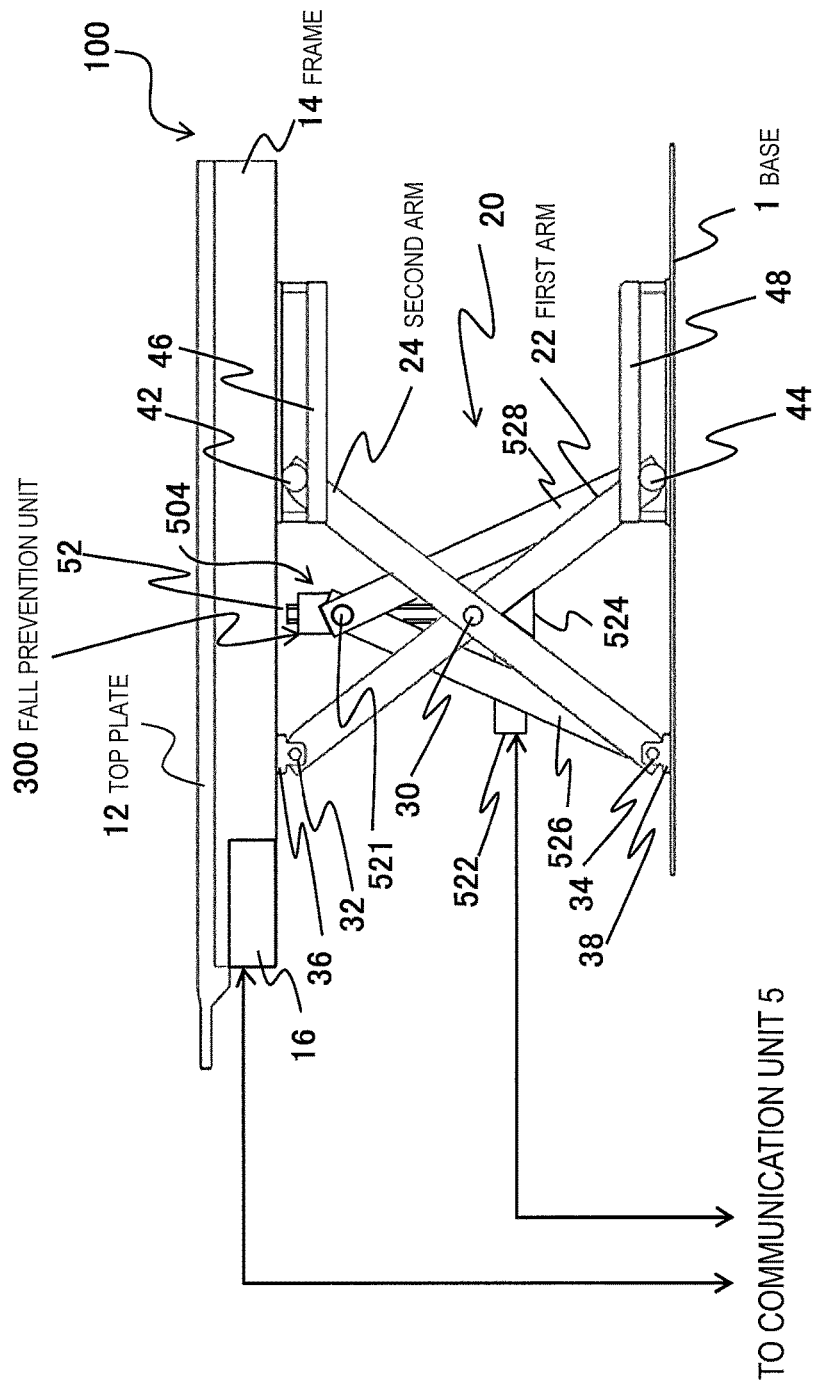
FIG. 18 is a schematic view illustrating an overall configuration of a bed provided in the medical image scanning system in still another embodiment of the invention.

FIG. 18 is a schematic view illustrating an overall configuration of a bed provided in the medical image scanning system in still another embodiment of the invention. The bed 100 for medical image scanning of this embodiment is configured to include a coupling pin 521 that joint-connects lift arms 526 and 528 rotatably on a vertical upper side of a center pin 30, and lower ends of the lift arms 526 and 528 are coupled to the base 1 so as to be rotatable by the rotating shaft 34 and the bearing 38 or the rotating shaft 44, respectively.

Additionally, a drive unit of the bed height adjustment unit 504 of this embodiment consists of a motor 522, a gear 524 driven by a motor 522, and the drive screw shaft 52 connected to the gear 524. The above-described fall prevention unit 300 is provided in a place where the fall prevention unit is threadedly engaged with the drive screw shaft 52.

By virtue of such a configuration, the same effects as the above-described effects can also be exhibited.

Figure 19:
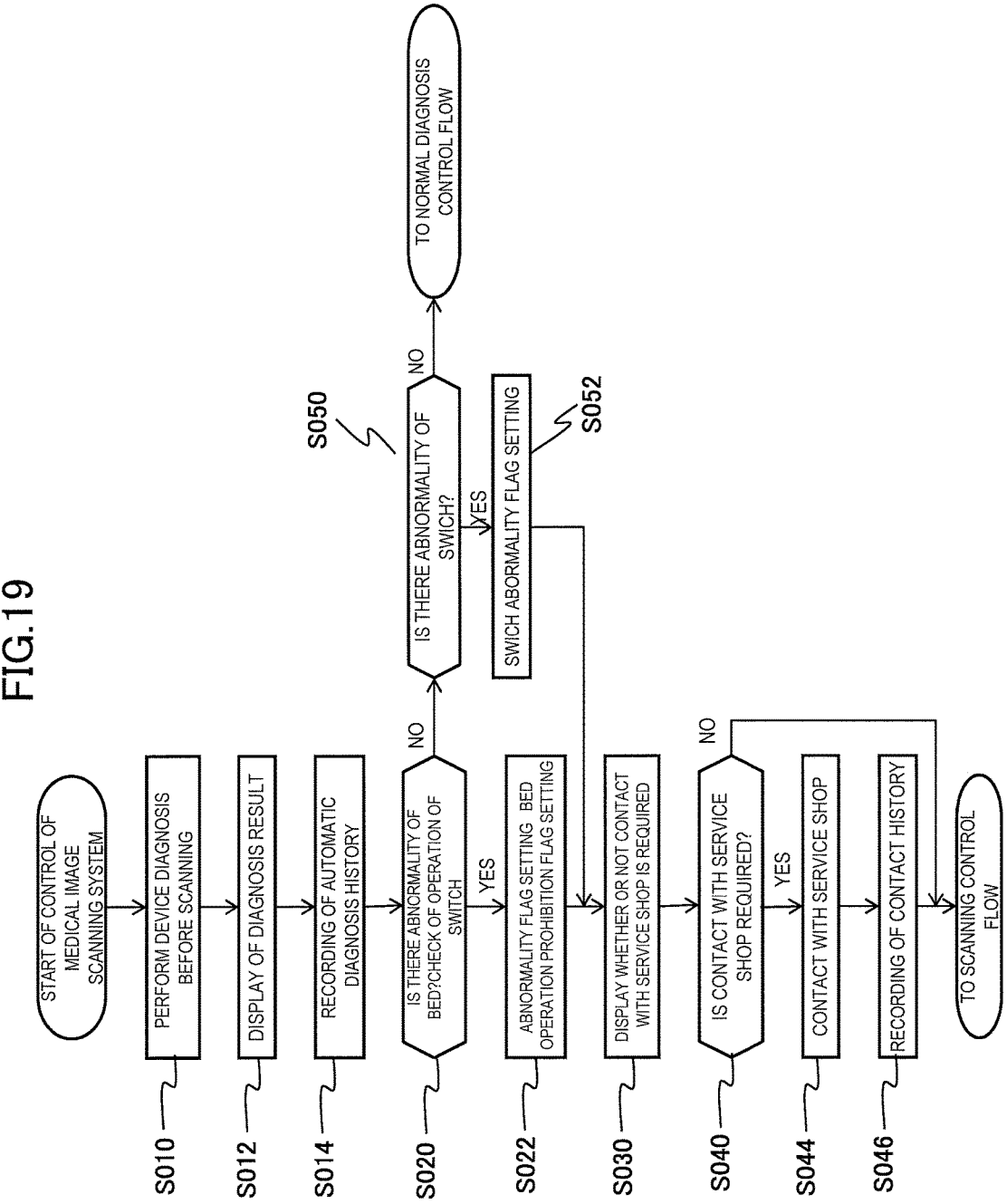
FIG. 19 is a flowchart illustrating the operation of abnormality diagnosis before scanning control start by a control unit of the medical image scanning system to which the bed for medical image scanning of the present embodiment is applied.

FIG. 19 is a flowchart illustrating the operation of abnormality diagnosis before scanning control start by the control unit of the medical image scanning system to which the bed for medical image scanning of the present embodiment is applied. This embodiment is an operation example of the medical image scanning system 200 to which the structures illustrated in FIGS. 8 to 14 are applied. According to an X-ray scanning situation when an abnormality has occurred, it is possible to give selection means for selecting which work will be performed next to an operator.

First, in Step S010, the control unit 110 performs the automatic diagnosis of devices of the medical image scanning system 200 before scanning. The control of the automatic diagnosis is performed by reading related control information from the various control programs 1430 of the storage unit 140.

Next, in Step S012, the control unit 110 displays diagnostic results on the display section 132 of the output unit 130. Additionally, in Step S014, the control unit 110 stores diagnosis history information in the bed automatic diagnosis history information group 1454 of the history information DB 1450 of the storage unit 40.

Next, in Step S020, the control unit 110 determines whether or not there is an abnormality in the bed 100 for medical image scanning. This is determined depending on above-described automatic diagnosis results or whether there is any operation in the above-described switch unit 152. The operation of the switch unit 152 is performed by receiving an abnormality signal based on the switch depression of the switch unit 152 via the communication unit 5.

Next, when it is determined that there is an abnormality, the control unit 110 sets abnormality flags and a bed operation prohibition flag in Step S022. The setting information of these flags is stored in the main storage unit 112 or the various-control-programs DE 1440. The control unit 110 performs the control of the drive unit 64 on the basis of the set flags. For example, the drive unit 64 is controlled so as to stop the rotation of the drive screw shaft 52 on the basis of the set flags. Accordingly, any damage to the bed or a device based on the rotation of the drive screw shaft 52 at the time of the occurrence of an abnormality can be prevented. The control unit 110 can also perform control so as to display a display showing the occurrence of the abnormality on the display section 132.

Additionally, when it is determined that there is no abnormality, in Step S050, the control unit 110 determines whether or not there is any abnormality, such as a failure, in the switch unit 152 itself. Here, with respect to the details of the configuration of determining whether or not there is any abnormality, such as a failure, in the switch unit 152 itself, the same components as those of the above-described embodiment will be designated by the same reference numeral, and the description thereof will be omitted.

Figure 20:
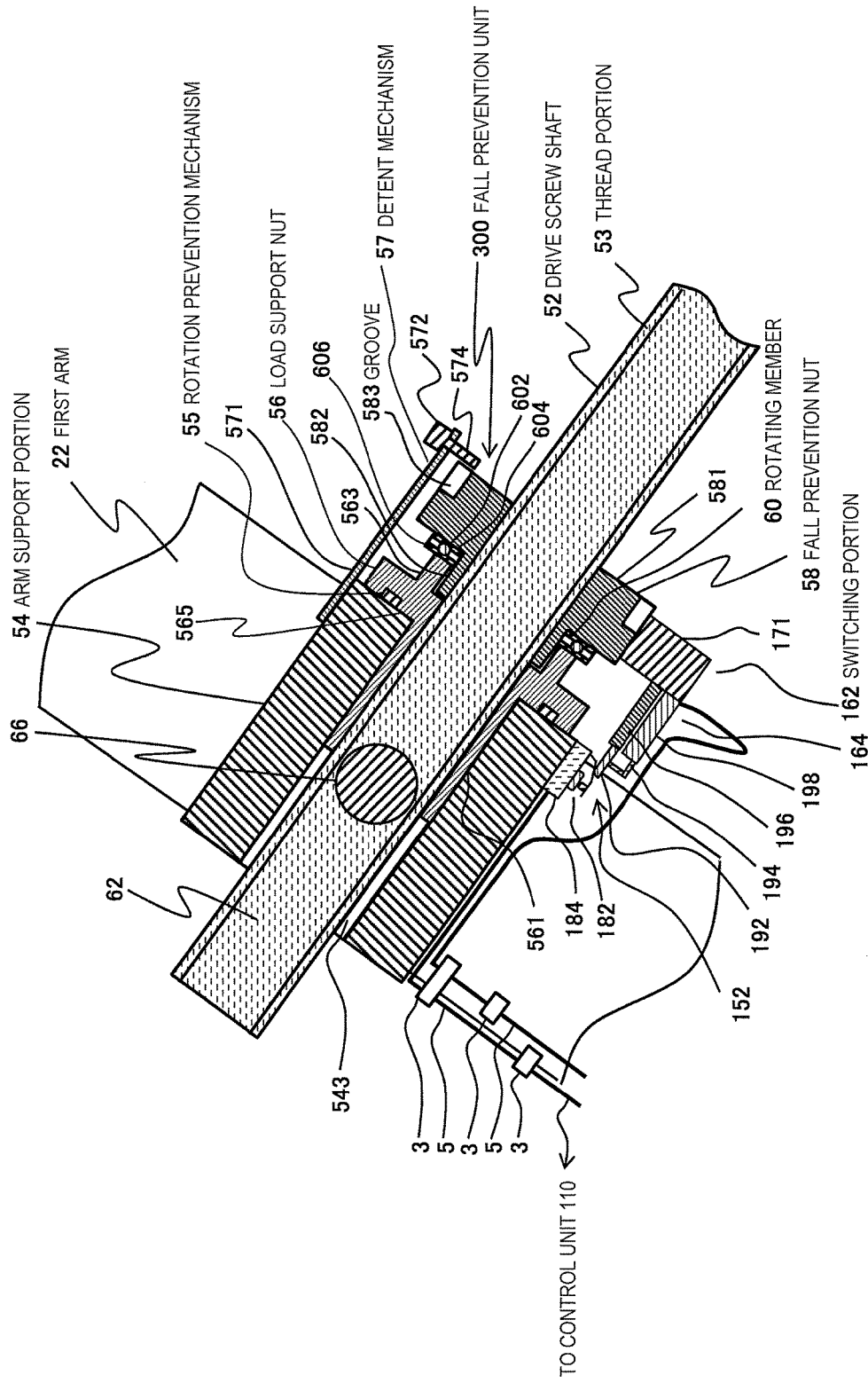
FIG. 20 is a longitudinal sectional view illustrating a detailed configuration of a fall prevention unit of the medical image scanning system provided with the bed on which an object is placed, in still another embodiment of the invention.

FIG. 20 is a longitudinal sectional view illustrating a detailed configuration of a fall prevention unit of the medical image scanning system provided with the bed on which an object is placed, in still another embodiment of the invention. This embodiment is an example in which the load support nut 56 is provided with the same switch unit 152 as the above-described switch unit, and the fall prevention nut 58 is provided with a switching portion 164 constituted of an electromagnetic relay consisting of a switch end 192, a coupling portion 194, a spring mechanism portion 196, an electromagnet portion 198 having an electromagnetic switch (not illustrated) therein, and the communication unit 5.

The switching portion 164 performs switching of the switch unit 152, and the switch end 192 is switch-depressed with this switching and the coupling portion 194 coupled to this switch end is also depressed. Accordingly, the electromagnetic switch within the electromagnet portion 198 is turned on. As a result, an electric current flows to an internal circuit (not illustrated), and a signal generated on the basis of this is transmitted to the control unit 110 via the communication unit 5.

According to this structure, even if generation of a signal by a malfunction, such as the damage of the switch unit 152 provided in the load support nut 56, does not occur, the signal generated by the above-described electromagnetic switch is sent to the control unit 110. Thus, even if the switch unit 152 does not operate normally, an operator can recognize that the load support nut 56 has fallen from the signal generated by the electromagnetic switch. Additionally, whether or not the switch unit 152 is damaged can also be confirmed by using the signal generated by this electromagnetic switch and the signal generated by the switching of the switch unit 152.

In Step S050, when the control unit 110 has determined the abnormality of the switch unit 152 by virtue of the above-described configuration and has determined that there is an abnormality, switch abnormality flags are set in Step S052, and the processing proceeds to Step S030 to be described below. The setting information of the switch abnormality flags are stored in the various-control-programs DB 1440.

Additionally, when there is no abnormality, the processing proceeds to Step S040 to be described below. Here, when the control unit 110 has determined that there is no abnormality in the switch unit 152, the processing proceeds to a normal diagnostic control flow. Additionally, the control unit 110 stores history information regarding having performed the abnormality diagnosis of the switch unit 152 in the storage unit 140. Then, the drive unit 64 is controlled to adjust the height of the top plate 12, and scanning for obtaining a medical image of an object is performed.

Next, in Step S030, the control unit 110 displays a display about whether or not the contact with service shops is required on the display section 132 of the output unit 130. This display may be a display about whether or not contacts are required, respectively, in correspondence with devices having abnormalities or may be a display about whether or not collective contacts are required, on the basis of the above set flag information.

Additionally, with respect to this display, whether or not contacts are required is selectable on the basis of an input performed by a person who operates the control unit, such as an operator, via the input unit 120. That is, the control unit 110 displays a display whether or not contacts with set service shops are required on the output unit 130, on the basis of the abnormality flags and the bed operation prohibition flag. For example, as illustrated in FIG. 22 to be described below, a display about whether or not contacts with service shops is displayed like service shop contact requirement information 1342 on a service shop contact requirement information display region 1340 of the display section 132.

Next, in Step S040, the control unit 110 determines whether or not contacts with service shops are required. Here, when the contacts are required, in Step S044, the control unit 110 makes contacts with service shops by immediately performing information communications showing device abnormalities and replacement part arrangements via the communication unit 5 to the service shops. Additionally, in Step S046, the history about contacts with service shops is stored as diagnosis history information in the service-shop contact history 1453 of the history information DB 1450 of the storage unit 140.

Additionally, in Step S040, the control unit 110 proceeds to the next scanning control flow to be described below when no contacts are required. In this case, with reference to the bed part replacement history information group 1451 and the bed maintenance history information group 1452 of the storage unit 140, a warning display showing that parts of devices are not replaced in a specific period or maintenance check is not performed, on the basis of the information groups, can be performed.

In this way, the control unit 110 performs a display showing abnormalities on the display section 132 on the basis of a signal generated by the switch unit 152, and the control unit 110 performs the control of causing the drive unit 64 to stop the rotation of the drive screw shaft 52.

Additionally, the control unit 110 confirms the operating state of the switch unit 152 for medical image scanning of the object, and determines whether or not the switch unit 152 itself is normal when it is determined that the fall prevention unit 300 is in a normal state.

The medical image scanning system to which the bed for medical image scanning of the present embodiment including the above configuration performs abnormality diagnosis through the above steps. Therefore, an operator can recognize the abnormalities of devices rapidly without overlooking failures of the devices and can also perform part replacement work rapidly. Thus, it is possible to provide a medical image scanning system that can rapidly perform detection and restoration of the abnormalities of the devices even in situations where handling is required as much as possible, such as during work related to medical checkups and the surgery of serious cases, can remarkably contribute to increases in efficiency and speed of medical service, and can rapidly respond to medical service, thereby more reliably maintaining an object's safety to improve the reliability of medical service.

Figure 21:
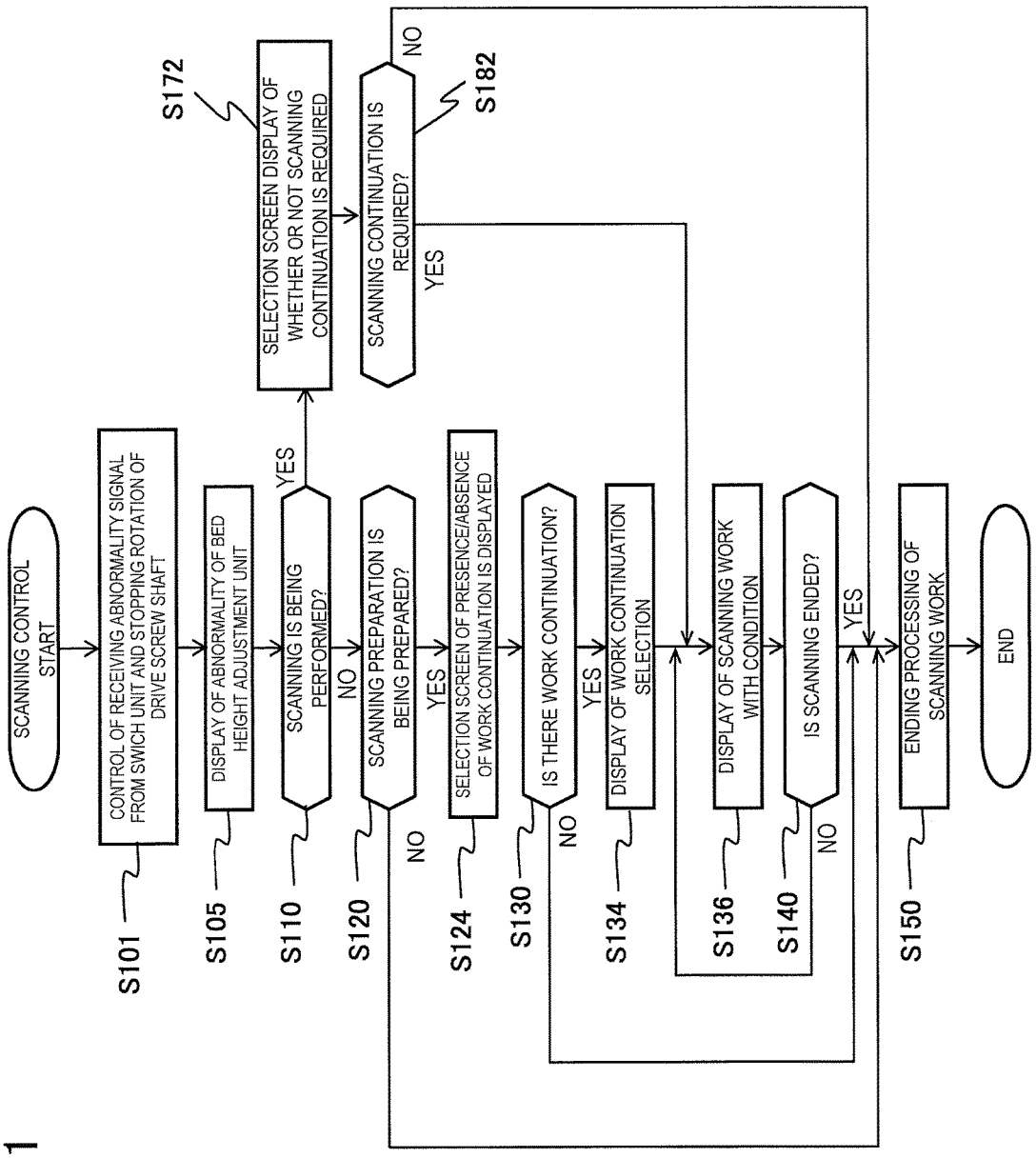
FIG. 21 is a flowchart illustrating the operation of abnormality diagnosis at the time of scanning control start by a control unit of a medical image scanning system to which the bed for medical image scanning of the present embodiment is applied.

FIG. 21 is a flowchart illustrating the operation of abnormality diagnosis at the time of scanning control start by the control unit of the medical image scanning system to which the bed for medical image scanning of the present embodiment is applied. Additionally, FIG. 22 is a view illustrating screen display at the time of the abnormality diagnosis of the medical image scanning system in FIGS. 20 and 21. The present embodiment is an operation example of the same medical image scanning system 200 as that in FIG. 20. The control unit 110 performs a screen display in which an operator is made to select whether or not work or continuation of scanning is required according to work or a scanning situation, and causes the operator to make a determination adapted to a situation or causes the operator to perform the control of the medical image scanning system 200 adapted to a situation.

First, in Step S101, the control unit 110 receives an abnormality signal, which is based on the falling of the load support nut 56 and generated by the switch depression of the switch unit 152, via the communication unit 5. Additionally similar to the example of the above-described FIG. 19, a control is performed so as to cause the drive unit 64 to stop the rotation of the drive screw shaft 52. Next, in Step S105, the control unit 110, as illustrated in FIG. 22, displays abnormality detection information 1322, showing that there is an abnormality in the bed height adjustment unit, on an abnormality detection information display region 1320 of the display section 132 of the output unit 130. Additionally, displays showing that continuation of work or scanning is warned of may be collectively performed.

Next, in Step S110, the control unit 110 determines whether or not scanning is being performed. The determination of whether or not scanning is being performed is possible by applying various determination means, such as detecting of whether or not there is any irradiation from an X-ray irradiation portion, receiving of a command signal for scanning execution, or receiving of an ending signal of completion of all scanning recording.

Next, when it is not determined that scanning is being performed, in Step S120, the control unit 110 determines whether or not scanning preparation is being performed. When scanning preparation is being performed, this step is in a state where a scanned image is not recorded and control of X-rays irradiation or the like is not performed, and can be, for example, a determination criterion about whether or not a scanning start command is output. When it is determined that scanning preparation is not being performed, this means the completion of scanning. Thus, the control unit 110 proceeds to Step S150 and performs ending processing of scanning work. Here, the ending processing of scanning work includes saving work, such saving of scanned images or work history, drive control of devices, such as driving of the top plate and the arms, drive unit stop work, such as stopping driving of the drive unit to stop a power source, or the like. The control unit 110 performs ending processing of these kinds of work, and ends the flow of the scanning control.

Additionally, when it is determined that scanning preparation is being performed, the control unit 110 proceeds to Step S124 where a selection screen of the presence/absence of work continuation is displayed like selection request information 1332 on a selection request information display region 1330 of the display section 132 of the output unit 130. Accordingly, the operator can select whether or not X-ray scanning is started as the work continuation or whether or not repairing is performed, such as whether or not work is stopped and parts of the fall prevention unit 300 are replaced according to an input to the input unit 120, for example, through the operation of a cursor 1350 performed by the operation of a pointing device.

Here, in Step S130, when it is determined that work continuation has been selected, the control unit 110 proceeds to Step S134, performs a display showing that operator's work continuation has been selected as the work continuation, and performs a display requesting the work continuation.

Then, when operator's work, such as preparation, is completed and scanning work is started, in Step S136, the control unit 110 performs the control of allowing the scanning work but limiting or prohibiting the lifting and lowering movement of the bed or performs displaying a display 1362 showing such a purport on the display section 132, and performs the display of requesting the operator to perform the scanning work.

Then, the control unit 110 proceeds to Step S140, and determines whether or not the scanning has been ended. Then, the control unit 110 proceeds to the above described Step S136 when it is determined that the scanning has not been ended, and proceeds to the above-described Step S150 when it is determined that the scanning has been ended.

Additionally, when the control unit 110 has determined in Step S110 that scanning is being performed, in Step S172, the control unit 110 displays a selection screen about whether scanning continuation is required or not on the display section 132 of the output unit 130, similar to the display of the selection screen of the presence/absence of the above-described work continuation. Accordingly, the operator can select whether or not X-ray scanning is started as the scanning continuation or whether or not repairing is performed, such as whether or not scanning is stopped and parts of the fall prevention unit 300 are replaced according to an input to the input unit 120, for example, through the operation of the cursor 1350 performed by the operation of a pointing device.

Additionally, whether or not the scanning continuation is required is determined in Step S182, and when it is determined that the scanning continuation is required on the basis of an operator's input as described above, the control unit 110 proceeds to above-described Step S136. Here, a work schedule is reviewed according to an instruction of scanning work continuation, and the scanning unit 210 is controlled according to the reviewed work schedule. Additionally, when it is determined that the scanning continuation is not required, the processing proceeds to the above-described Step S150. Here, according to an instruction that stops the scanning work, the ending processing of work is performed and the history of a working state is stored.

In this way, the control unit 110 performs a display for selecting the presence/absence of scanning work continuation on the display section 132 on the basis of a signal generated by the switch unit 152, and the control unit 110 performs ending processing of work and stores the history of a working state, according to an instruction that stops scanning work.

Additionally, the control unit 110 performs a display for selecting the presence/absence of scanning work continuation on the display section 132 on the basis of a signal generated by the switch unit 152, and the control unit 110 performs review of a work schedule according to an instruction of scanning work continuation, and controls the scanning unit 210 according to the reviewed work schedule.

Additionally, as described above, an abnormality diagnosis method in the medical image scanning system 200 of the present embodiment includes a step in which the control unit 110 confirms the operating state of the switch unit 152, a step in which the control unit determines that the fall prevention unit is normal on the basis of the operating state of the switch unit 152, a step in which the control unit determine whether or not the switch unit 152 itself is normal when it is determined that the fall prevention unit 300 is in a normal state, and a step in which the control unit controls the drive unit 64 to adjust the height of the top plate 12, and performs scanning for obtaining a medical image of an object when it is determined that the switch unit 152 itself is normal.

As described above, the bed 100 for medical image scanning of the present embodiment is applied to the medical image scanning system 200. Accordingly, when the load support nut 56 has fallen, this can be immediately recognized as being abnormal by the medical image scanning system 200, and an operator can appropriately select whether or not scanning or preparation is continued according to a scanning situation. Thus, it is possible to provide a medical image scanning system provided with a bed on which an object is placed, which can perform efficient scanning and medical service while an object's safety is maintained.

The medical image scanning system provided with the bed for medical image scanning of the present embodiment can also be applied to structures other than the structures of the above-described embodiments and can exhibit the same effects as the effects of the above-described embodiments, if the above-described fall prevention unit can be applied.

REFERENCE SIGNS LIST

1: BASE
5: COMMUNICATION UNIT
12: TOP PLATE
14: FRAME
20: ARM
22: FIRST ARM
24: SECOND ARM
50: BED HEIGHT ADJUSTMENT UNIT
52: DRIVE SCREW SHAFT
54: ARM SUPPORT PORTION
55: ROTATION PREVENTION MECHANISM
56: LOAD SUPPORT NUT
57: DETENT MECHANISM
58: FALL PREVENTION NUT
60: ROTATING MEMBER
62: END
64: DRIVE UNIT
66: COUPLING FIXING PORTION
72: ROLLING BEARING
100: BED FOR MEDICAL IMAGE SCANNING
110: CONTROL UNIT
120: INPUT UNIT
130: OUTPUT UNIT
132: DISPLAY SECTION
140: STORAGE UNIT
150: EXTERNAL COUPLING UNIT
15: SWITCH UNIT
162: SWITCHING PORTION
172: PUSHING AND STRIKING PORTION
173: CAM
174: SLIDING MEMBER
175: ELASTIC MEMBER
200: MEDICAL IMAGE SCANNING SYSTEM
210: SCANNING UNIT
250: DOWNWARD DIRECTION
300: FALL PREVENTION UNIT
502: BED HEIGHT ADJUSTMENT UNIT
504: BED HEIGHT ADJUSTMENT UNIT
541: INNER CYLINDER
542: OUTER CYLINDER
571: HOLDER
572: DETENT
574: END
581: HEAD
582: HOLDER
583: GROOVE
584: GROOVE
588: LATERAL PORTION
589: LATERAL PORTION
602: BALL
604: RING
606: RING
1320: ABNORMALITY DETECTION INFORMATION DISPLAY REGION
1330: SELECTION REQUEST DISPLAY REGION
1340: SERVICE SHOP CONTACT REQUIREMENT INFORMATION DISPLAY REGION
1350: CURSOR
1450: HISTORY INFORMATION DB
D: DISTANCE BETWEEN LOAD SUPPORT NUT AND ROTATING MEMBER

The invention claimed is:

1. A medical image scanning system provided with a bed, the medical image scanning system comprising:
a top plate on which an object is placed;
an arm that supports the top plate;
a drive screw shaft;
a fall prevention unit including a load support nut that is threadedly engaged with the drive screw shaft and to which the load of the top plate is applied, and a fall prevention nut that is arranged below the load support nut and is threadedly engaged with the drive screw shaft;
a rotating member is provided between the load support nut and the fall prevention nut;
a drive unit configured to rotate the drive screw shaft to change a distance from the fall prevention unit, thereby changing the height of the top plate;
a scanning unit that performs scanning for obtaining a medical image of the object;
a display section that displays the medical image; and
a control unit that controls the drive unit to adjust the height of the top plate, and controls the scanning unit to perform scanning for obtaining a medical image, wherein:
the fall prevention unit includes a detent mechanism that performs the turning stop of the fall prevention nut and that releases the turning stop of the fall prevention nut when the threaded engagement between the drive screw shaft and the load support nut is disconnected, the fall prevention nut supports the rotating member and the rotating member supports the load support nut in a state where the threaded engagement between the drive screw shaft and the load support nut is disconnected; and a rolling friction force between the load support nut and the fall prevention nut is smaller than a sliding friction force between the fall prevention nut and the drive screw shaft.

2. The medical image scanning system provided with a bed according to claim 1, wherein the rotating member is a rolling bearing.

3. The medical image scanning system provided with a bed according to claim 1, wherein the rotating member has a first member and a second member including surfaces that closely face each other and supports the first member and the second member so as to be mutually rotatable, the fall prevention nut supports the first member, the first member rotatably supports the second member, and the second member supports the load support nut, in a state where the threaded engagement between the drive screw shaft and the load support nut is disconnected, and a frictional force between the first member and the second member is smaller than a sliding friction force between the fall prevention nut and the drive screw shaft.

4. The medical image scanning system provided with a bed according to claim 3, further comprising:

a low friction material including molybdenum provided between the first member and the second member.

* * * * *